(12) United States Patent
Peterson et al.

(10) Patent No.: US 10,646,198 B2
(45) Date of Patent: May 12, 2020

(54) INTRAVASCULAR IMAGING AND GUIDE CATHETER DETECTION METHODS AND SYSTEMS

(71) Applicant: LIGHTLAB IMAGING, INC., Westford, MA (US)

(72) Inventors: James G. Peterson, Yarmouth, ME (US); Christopher E. Griffin, Wilton, NH (US); Sonal Ambwani, Westborough, MA (US)

(73) Assignee: LIGHTLAB IMAGING, INC., Westford, MA (US)

(*) Notice: Subject to any disclaimer, the term of this patent is extended or adjusted under 35 U.S.C. 154(b) by 877 days.

(21) Appl. No.: 14/974,856

(22) Filed: Dec. 18, 2015

(65) Prior Publication Data

US 2017/0143296 A1     May 25, 2017

Related U.S. Application Data

(60) Provisional application No. 62/257,662, filed on Nov. 19, 2015.

(51) Int. Cl.
  *A61B 8/12*     (2006.01)
  *A61B 5/00*     (2006.01)
  (Continued)

(52) U.S. Cl.
  CPC ............ *A61B 8/12* (2013.01); *A61B 5/0035* (2013.01); *A61B 5/0066* (2013.01); *A61B 5/0084* (2013.01); *A61B 5/02007* (2013.01); *A61B 5/061* (2013.01); *A61B 5/6852* (2013.01); *A61B 90/36* (2016.02); *G06T 7/73* (2017.01); *G06T 2207/10101* (2013.01); *G06T 2207/30021* (2013.01)

(58) Field of Classification Search
CPC combination set(s) only.
See application file for complete search history.

(56) References Cited

U.S. PATENT DOCUMENTS

| | | |
|---|---|---|
| 4,548,473 A | 10/1985 | Lo et al. |
| 5,054,492 A | 10/1991 | Scribner et al. |

(Continued)

FOREIGN PATENT DOCUMENTS

| | | |
|---|---|---|
| EP | 2062526 | 5/2009 |
| JP | 63-127201 | 5/1988 |

(Continued)

OTHER PUBLICATIONS

Wang et al., "Fully automated side branch detection in intravascular optical coherence tomography pullback runs", Biomedical Optics Express, vol. 5, No. 9, Aug. 25, 2014, pp. 3160-3173. (Year: 2014).*

(Continued)

*Primary Examiner* — Katherine L Fernandez
(74) *Attorney, Agent, or Firm* — K&L Gates LLP

(57) ABSTRACT

In part, the disclosure relates to computer-based methods, devices, and systems suitable for detecting a delivery catheter using intravascular data. In one embodiment, the delivery catheter is used to position the intravascular data collection probe. The probe can collect data suitable for generating one or more representations of a blood vessel with respect to which the delivery catheter can be detected.

6 Claims, 11 Drawing Sheets

(51) Int. Cl.
  *A61B 5/06* (2006.01)
  *A61B 5/02* (2006.01)
  *G06T 7/73* (2017.01)
  *A61B 90/00* (2016.01)

(56) References Cited

U.S. PATENT DOCUMENTS

| | | |
|---|---|---|
| 5,321,501 A | 6/1994 | Swanson et al. |
| 5,459,570 A | 10/1995 | Swanson et al. |
| 5,465,147 A | 11/1995 | Swanson |
| 5,477,858 A | 12/1995 | Norris et al. |
| 5,488,674 A | 1/1996 | Burt et al. |
| 5,509,093 A | 4/1996 | Miller et al. |
| 5,518,810 A | 5/1996 | Nishihara et al. |
| 5,531,227 A | 7/1996 | Schneider |
| 5,586,201 A | 12/1996 | Whiting et al. |
| 5,619,368 A | 4/1997 | Swanson |
| 5,632,767 A | 5/1997 | Sinofsky |
| 5,643,253 A | 7/1997 | Baxter et al. |
| 5,662,109 A | 9/1997 | Hutson |
| 5,715,827 A | 2/1998 | Corl et al. |
| 5,748,598 A | 5/1998 | Swanson et al. |
| 5,771,895 A | 6/1998 | Slager |
| 5,784,352 A | 7/1998 | Swanson et al. |
| 5,797,849 A | 8/1998 | Vesely et al. |
| 5,822,391 A | 10/1998 | Whitting |
| 5,908,415 A | 6/1999 | Sinofsky |
| 5,947,959 A | 9/1999 | Sinofsky |
| 5,956,355 A | 9/1999 | Swanson et al. |
| 5,989,189 A | 11/1999 | LeBlanc et al. |
| 6,111,645 A | 8/2000 | Tearney et al. |
| 6,134,003 A | 10/2000 | Tearney et al. |
| 6,148,095 A | 11/2000 | Prause et al. |
| 6,160,826 A | 12/2000 | Swanson et al. |
| 6,191,862 B1 | 2/2001 | Swanson et al. |
| 6,195,445 B1 | 2/2001 | Jolly et al. |
| 6,208,883 B1 | 3/2001 | Holupka et al. |
| 6,270,492 B1 | 8/2001 | Sinofsky |
| 6,282,011 B1 | 8/2001 | Tearney et al. |
| 6,302,875 B1 | 10/2001 | Makower et al. |
| 6,348,960 B1 | 2/2002 | Etori et al. |
| 6,381,350 B1 | 4/2002 | Klingensmith et al. |
| 6,385,332 B1 | 5/2002 | Zahalka et al. |
| 6,421,164 B2 | 7/2002 | Tearney et al. |
| 6,445,939 B1 | 9/2002 | Swanson et al. |
| 6,471,656 B1 | 10/2002 | Shalman et al. |
| 6,485,413 B1 | 11/2002 | Boppart et al. |
| 6,501,551 B1 | 12/2002 | Tearney et al. |
| 6,552,796 B2 | 4/2003 | Magnin et al. |
| 6,564,087 B1 | 5/2003 | Pitris et al. |
| 6,565,514 B2 | 5/2003 | Svanerudh et al. |
| 6,570,659 B2 | 5/2003 | Schmitt |
| 6,585,660 B2 | 7/2003 | Dorando et al. |
| 6,692,824 B2 | 2/2004 | Benz et al. |
| 6,697,667 B1 | 2/2004 | Lee et al. |
| 6,706,004 B2 | 3/2004 | Tearney et al. |
| 6,716,178 B1 | 4/2004 | Kilpatrick et al. |
| 6,718,089 B2 | 4/2004 | James et al. |
| 6,728,566 B1 | 4/2004 | Subramanyan et al. |
| 6,731,973 B2 | 5/2004 | Voith |
| 6,760,112 B2 | 7/2004 | Reed et al. |
| 6,785,409 B1 | 8/2004 | Suri |
| 6,868,736 B2 | 3/2005 | Sawatari et al. |
| 6,879,851 B2 | 4/2005 | McNamara et al. |
| 6,891,984 B2 | 5/2005 | Petersen et al. |
| 6,932,809 B2 | 8/2005 | Sinofsky |
| 6,937,696 B1 | 8/2005 | Mostafavi |
| 6,942,657 B2 | 9/2005 | Sinofsky et al. |
| 6,947,040 B2 | 9/2005 | Tek et al. |
| 6,973,202 B2 | 12/2005 | Mostafavi |
| 6,974,557 B1 | 12/2005 | Webler et al. |
| 7,068,831 B2 | 6/2006 | Florent et al. |
| 7,134,994 B2 | 11/2006 | Alpert et al. |
| 7,191,100 B2 | 3/2007 | Mostafavi |
| 7,208,333 B2 | 4/2007 | Flanders et al. |
| 7,231,243 B2 | 6/2007 | Tearney et al. |
| 7,241,286 B2 | 7/2007 | Atlas |
| 7,298,478 B2 | 11/2007 | Gilbert et al. |
| 7,301,644 B2 | 11/2007 | Knighton et al. |
| 7,321,677 B2 | 1/2008 | Evron et al. |
| 7,329,223 B1 | 2/2008 | Ainsworth et al. |
| 7,355,699 B2 | 4/2008 | Gilbert et al. |
| 7,359,554 B2 | 4/2008 | Klingensmith et al. |
| 7,397,935 B2 | 7/2008 | Kimmel et al. |
| 7,408,648 B2 | 8/2008 | Kleen et al. |
| 7,412,141 B2 | 8/2008 | Gowda et al. |
| 7,414,779 B2 | 8/2008 | Huber et al. |
| 7,415,049 B2 | 8/2008 | Flanders et al. |
| 7,450,241 B2 | 11/2008 | Zuluaga |
| RE40,608 E | 12/2008 | Glover et al. |
| 7,492,522 B2 | 2/2009 | Gilbert et al. |
| 7,532,920 B1 | 5/2009 | Ainsworth et al. |
| 7,576,861 B2 | 8/2009 | Gilbert et al. |
| 7,593,559 B2 | 9/2009 | Toth et al. |
| 7,610,081 B2 | 10/2009 | Redel |
| 7,619,646 B2 | 11/2009 | Freifeld et al. |
| 7,625,366 B2 | 12/2009 | Atlas |
| 7,627,156 B2 | 12/2009 | Margolis et al. |
| 7,650,179 B2 | 1/2010 | Redel et al. |
| 7,679,754 B2 | 3/2010 | Zuluaga |
| 7,697,972 B2 | 4/2010 | Verard et al. |
| 7,706,585 B2 | 4/2010 | Kleen |
| 7,711,413 B2 | 5/2010 | Feldman et al. |
| 7,729,746 B2 | 6/2010 | Redel et al. |
| 7,733,497 B2 | 6/2010 | Yun et al. |
| 7,742,797 B2 | 6/2010 | Redel et al. |
| 7,783,337 B2 | 8/2010 | Feldman et al. |
| 7,783,338 B2 | 8/2010 | Ainsworth et al. |
| 7,785,286 B2 | 8/2010 | Magnin et al. |
| 7,792,342 B2 | 9/2010 | Barbu et al. |
| 7,801,343 B2 | 9/2010 | Unal et al. |
| 7,813,609 B2 | 10/2010 | Petersen et al. |
| 7,831,078 B2 | 11/2010 | Unal et al. |
| 7,843,976 B2 | 11/2010 | Cable et al. |
| 7,848,791 B2 | 12/2010 | Schmitt et al. |
| 7,853,316 B2 | 12/2010 | Milner et al. |
| 7,869,663 B2 | 1/2011 | Buckland et al. |
| 7,872,759 B2 | 1/2011 | Tearney et al. |
| 7,916,387 B2 | 3/2011 | Schmitt |
| 7,918,793 B2 | 4/2011 | Altmann et al. |
| 7,925,327 B2 | 4/2011 | Weese |
| 7,930,014 B2 | 4/2011 | Huennekens et al. |
| 7,935,060 B2 | 5/2011 | Schmitt et al. |
| 7,967,743 B2 | 6/2011 | Ishihara |
| 7,988,633 B2 | 8/2011 | Hossack et al. |
| 7,991,105 B2 | 8/2011 | Mielekamp et al. |
| 8,029,447 B2 | 10/2011 | Kanz et al. |
| 8,116,605 B2 | 2/2012 | Petersen et al. |
| 8,206,374 B2 | 6/2012 | Duane et al. |
| 8,206,377 B2 | 6/2012 | Petroff |
| 8,208,995 B2 | 6/2012 | Tearney et al. |
| 8,223,143 B2 | 7/2012 | Dastmalchi et al. |
| 8,259,303 B2 | 9/2012 | Johnson et al. |
| 8,290,228 B2 | 10/2012 | Cohen et al. |
| 8,298,147 B2 | 10/2012 | Huennekens et al. |
| 8,315,282 B2 | 11/2012 | Huber et al. |
| 8,325,419 B2 | 12/2012 | Schmitt |
| 8,351,665 B2 | 1/2013 | Tearney et al. |
| 8,358,461 B2 | 1/2013 | Huber et al. |
| 8,423,121 B2 | 4/2013 | Wang et al. |
| 8,449,468 B2 | 5/2013 | Petersen et al. |
| 8,457,375 B2 | 6/2013 | Rieber et al. |
| 8,457,440 B1 | 6/2013 | Johnson |
| 8,463,007 B2 | 6/2013 | Steinberg et al. |
| 8,478,384 B2 | 7/2013 | Schmitt et al. |
| 8,478,387 B2 | 7/2013 | Xu |
| 8,503,844 B2 | 8/2013 | Petersen et al. |
| 8,542,900 B2 | 9/2013 | Tolkowsky et al. |
| 8,556,820 B2 | 10/2013 | Alpert et al. |
| 8,562,537 B2 | 10/2013 | Alpert et al. |
| 8,571,639 B2 | 10/2013 | Mostafavi |
| 8,581,643 B1 | 11/2013 | Schmitt |
| 8,582,109 B1 | 11/2013 | Schmitt |
| 8,582,619 B2 | 11/2013 | Adler |

(56) References Cited

U.S. PATENT DOCUMENTS

| | | |
|---|---|---|
| 8,582,934 B2 | 11/2013 | Adler et al. |
| 8,670,603 B2 | 3/2014 | Tolkowsky et al. |
| 8,687,201 B2 | 4/2014 | Adler |
| 8,693,756 B2 | 4/2014 | Tolkowsky et al. |
| 8,700,130 B2 | 4/2014 | Iddan et al. |
| 8,781,193 B2 | 7/2014 | Steinberg et al. |
| 8,786,336 B1 | 7/2014 | Schmitt |
| 8,831,321 B1 | 9/2014 | Elbasiony |
| 8,855,744 B2 | 10/2014 | Tolkowsky et al. |
| 8,909,323 B2 | 12/2014 | Baumgart |
| 8,913,084 B2 | 12/2014 | Chen et al. |
| 8,948,228 B2 | 2/2015 | Adler |
| 8,953,911 B1 | 2/2015 | Xu et al. |
| 8,983,580 B2 | 3/2015 | Boppart et al. |
| 9,069,396 B2 | 6/2015 | Adler et al. |
| 9,173,591 B2 | 11/2015 | Elbasiony |
| 9,308,052 B2 | 4/2016 | Tolkowsky et al. |
| 9,351,698 B2 | 5/2016 | Dascal et al. |
| 9,404,731 B2 | 8/2016 | Adler et al. |
| 9,435,956 B1 | 9/2016 | Xu et al. |
| 9,488,464 B1 | 11/2016 | Schmitt |
| 9,629,571 B2 | 4/2017 | Tolkowsky et al. |
| 2002/0115931 A1 | 8/2002 | Strauss et al. |
| 2002/0161351 A1 | 10/2002 | Samson et al. |
| 2004/0006277 A1 | 1/2004 | Langenhove et al. |
| 2005/0043614 A1 | 2/2005 | Huizenga et al. |
| 2005/0201662 A1 | 9/2005 | Petersen et al. |
| 2005/0238067 A1 | 10/2005 | Choi |
| 2005/0249391 A1 | 11/2005 | Kimmel et al. |
| 2006/0095065 A1 | 5/2006 | Tanimura et al. |
| 2006/0135870 A1 | 6/2006 | Webler |
| 2006/0165270 A1 | 7/2006 | Borgert et al. |
| 2006/0187537 A1 | 8/2006 | Huber et al. |
| 2006/0203859 A1 | 9/2006 | Cable et al. |
| 2006/0241465 A1 | 10/2006 | Huennekens et al. |
| 2006/0241503 A1 | 10/2006 | Schmitt et al. |
| 2006/0244973 A1 | 11/2006 | Yun et al. |
| 2007/0024617 A1 | 2/2007 | Poole |
| 2007/0060822 A1 | 3/2007 | Alpert et al. |
| 2007/0066890 A1 | 3/2007 | Maschke |
| 2007/0115481 A1 | 5/2007 | Toth et al. |
| 2007/0123771 A1 | 5/2007 | Redel et al. |
| 2007/0135803 A1 | 6/2007 | Belson |
| 2007/0165916 A1 | 7/2007 | Cloutier et al. |
| 2007/0167710 A1 | 7/2007 | Unal et al. |
| 2007/0232933 A1 | 10/2007 | Gille et al. |
| 2007/0260198 A1 | 11/2007 | Atlas |
| 2007/0293932 A1 | 12/2007 | Zilla et al. |
| 2008/0100612 A1 | 5/2008 | Dastmalchi et al. |
| 2008/0161696 A1 | 7/2008 | Schmitt et al. |
| 2008/0165366 A1 | 7/2008 | Schmitt et al. |
| 2008/0221439 A1 | 9/2008 | Iddan et al. |
| 2008/0221440 A1 | 9/2008 | Iddan et al. |
| 2008/0221442 A1 | 9/2008 | Tolkowsky et al. |
| 2008/0228086 A1 | 9/2008 | Ilegbusi et al. |
| 2008/0281205 A1 | 11/2008 | Naghavi et al. |
| 2009/0027051 A1 | 1/2009 | Stuber et al. |
| 2009/0174931 A1 | 7/2009 | Huber et al. |
| 2009/0204134 A1 | 8/2009 | Kassab |
| 2009/0306520 A1 | 12/2009 | Schmitt et al. |
| 2010/0076320 A1 | 3/2010 | Petersen et al. |
| 2010/0094127 A1 | 4/2010 | Xu |
| 2010/0157041 A1 | 6/2010 | Klaiman et al. |
| 2010/0160764 A1 | 6/2010 | Steinberg et al. |
| 2010/0160773 A1 | 6/2010 | Cohen et al. |
| 2010/0161023 A1 | 6/2010 | Cohen et al. |
| 2010/0172556 A1 | 7/2010 | Cohen et al. |
| 2010/0191102 A1 | 7/2010 | Steinberg et al. |
| 2010/0222671 A1 | 9/2010 | Cohen et al. |
| 2010/0228076 A1 | 9/2010 | Blank et al. |
| 2010/0253949 A1 | 10/2010 | Adler et al. |
| 2011/0007315 A1 | 1/2011 | Petersen et al. |
| 2011/0071404 A1 | 3/2011 | Schmitt et al. |
| 2011/0071405 A1 | 3/2011 | Judell et al. |
| 2011/0101207 A1 | 5/2011 | Schmitt |
| 2011/0151980 A1 | 6/2011 | Petroff |
| 2011/0157686 A1 | 6/2011 | Huber et al. |
| 2011/0172511 A1 | 7/2011 | Schmitt et al. |
| 2011/0178413 A1 | 7/2011 | Schmitt et al. |
| 2011/0190586 A1 | 8/2011 | Kemp |
| 2011/0216325 A1 | 9/2011 | Schmitt |
| 2011/0228280 A1 | 9/2011 | Schmitt et al. |
| 2011/0230758 A1 | 9/2011 | Eichler |
| 2011/0237958 A1 | 9/2011 | Onimura |
| 2011/0257545 A1 | 10/2011 | Suri |
| 2011/0319752 A1 | 12/2011 | Steinberg et al. |
| 2012/0004529 A1 | 1/2012 | Tolkowsky et al. |
| 2012/0029339 A1 | 2/2012 | Cohen et al. |
| 2012/0057157 A1 | 3/2012 | Petersen et al. |
| 2012/0075638 A1 | 3/2012 | Rollins et al. |
| 2012/0162660 A1 | 6/2012 | Kemp |
| 2012/0310081 A1 | 6/2012 | Adler et al. |
| 2012/0224751 A1 | 9/2012 | Kemp et al. |
| 2012/0236883 A1 | 9/2012 | Adler |
| 2012/0238869 A1 | 9/2012 | Schmitt et al. |
| 2012/0250028 A1 | 10/2012 | Schmitt et al. |
| 2012/0300215 A1 | 11/2012 | Johnson et al. |
| 2012/0300216 A1 | 11/2012 | Johnson et al. |
| 2013/0006105 A1 | 1/2013 | Furuichi |
| 2013/0010303 A1 | 1/2013 | Petersen et al. |
| 2013/0012811 A1 | 1/2013 | Schmitt et al. |
| 2013/0023761 A1 | 1/2013 | Petroff |
| 2013/0051728 A1 | 2/2013 | Petroff |
| 2013/0072805 A1 | 3/2013 | Schmitt et al. |
| 2013/0123616 A1 | 5/2013 | Merritt et al. |
| 2013/0242258 A1* | 9/2013 | Higuchi ............ G01B 9/02064 351/206 |
| 2013/0303910 A1 | 11/2013 | Hubbard et al. |
| 2013/0310698 A1 | 11/2013 | Judell et al. |
| 2014/0018669 A1 | 1/2014 | Xu |
| 2014/0024931 A1 | 1/2014 | Winston et al. |
| 2014/0094660 A1 | 4/2014 | Tolkowsky et al. |
| 2014/0094689 A1 | 4/2014 | Cohen et al. |
| 2014/0094691 A1 | 4/2014 | Steinberg et al. |
| 2014/0094692 A1 | 4/2014 | Tolkowsky et al. |
| 2014/0094693 A1 | 4/2014 | Cohen et al. |
| 2014/0094697 A1 | 4/2014 | Petroff et al. |
| 2014/0114182 A1 | 4/2014 | Petersen et al. |
| 2014/0114184 A1 | 4/2014 | Klaiman et al. |
| 2014/0114185 A1 | 4/2014 | Tolkowsky et al. |
| 2014/0142427 A1 | 5/2014 | Petroff |
| 2014/0142432 A1 | 5/2014 | Hutchins et al. |
| 2014/0142436 A1 | 5/2014 | Hutchins et al. |
| 2014/0187929 A1 | 7/2014 | Schmitt et al. |
| 2014/0218742 A1 | 8/2014 | Adler |
| 2014/0249407 A1 | 9/2014 | Adler et al. |
| 2014/0268167 A1 | 9/2014 | Friedman et al. |
| 2014/0270445 A1 | 9/2014 | Kemp |
| 2014/0276011 A1 | 9/2014 | Schmitt et al. |
| 2014/0276020 A1 | 9/2014 | Hutchins et al. |
| 2014/0309536 A1 | 10/2014 | Douk et al. |
| 2014/0379269 A1 | 12/2014 | Schmitt |
| 2015/0153157 A1 | 6/2015 | Schmitt et al. |
| 2015/0119707 A1 | 7/2015 | Schmitt |
| 2015/0192405 A1 | 7/2015 | Schmitt |
| 2015/0297373 A1 | 10/2015 | Schmitt et al. |
| 2015/0370229 A1 | 12/2015 | Adler et al. |
| 2016/0000406 A1 | 1/2016 | Petroff |
| 2016/0022208 A1 | 1/2016 | Gopinath |
| 2016/0058307 A1 | 3/2016 | Svanerudh |
| 2016/0070066 A1 | 3/2016 | Schmitt et al. |
| 2016/0073885 A1 | 3/2016 | Adler |
| 2016/0174925 A1 | 6/2016 | Dascal et al. |
| 2016/0174932 A1* | 6/2016 | Katsuyama ......... G01S 15/8915 600/424 |
| 2016/0313507 A1 | 10/2016 | Adler et al. |
| 2016/0335763 A1 | 11/2016 | Ambwani et al. |
| 2016/0335766 A1 | 11/2016 | Ambwani et al. |

FOREIGN PATENT DOCUMENTS

| | | |
|---|---|---|
| WO | 2006076409 | 7/2006 |
| WO | 2007002685 | 1/2007 |
| WO | 2011038044 | 3/2011 |

(56) References Cited

FOREIGN PATENT DOCUMENTS

| WO | 2012176191 | 12/2012 |
|---|---|---|
| WO | 2013175472 | 11/2013 |
| WO | 2014002095 | 3/2014 |
| WO | 2014175853 | 10/2014 |

OTHER PUBLICATIONS

Wang et al., "Automatic stent strut detection in intravascular optical coherence tomographic pullback runs", Int J. Cardiovascular Imaging, vol. 29, 2013, pp. 29-38. (Year: 2013).*

Briguori et al., "Intravascular ultrasound criteria for the assessment of the functional significance of intermediate coronary artery stenoses and comparison with fractional flow reserve," Am J. Cardiol 87:136-141, 2001.

Kassab et al., "The pattern of coronary arteriolar bifurcations and the uniform shear hypothesis," Annals of Biomedical Engineering 23 (1): 13-20, 1995.

Hariri et al., "An automatic image processing algorithm for initiating and terminating intracoronary OFDI pullback" Biomedical Optics Express 1:2 566-573 (Sep. 1, 2010).

Harrison et al., "The value of lesion cross-sectional area determined by quantitative coronary angiography in assessing the physiologic significance of proximal left anterior descending coronary arterial stenoses," Circulation 69:6 1111-1119, 1984.

Kirkeeide, "Coronary obstructions, morphology, and physiological significance," in Reiber JHC and Serruys PW (eds.), Quantitative Coronary Arteriography, Kluwer Academic Publishers, the Netherlands, 1991, pp. 229-244.

Kolyva et al., "Increased diastolic time fraction as beneficial adjunct of α1-adrenergic receptor blockade after percutaneous coronary intervention," Am J Physiol Heart Circ Physiol 295: H2054-H2060, 2008.

Kolyva et al., "'Windkesselness' of coronary arteries hampers assessment of human coronary wave speed by single-point technique," Am J Physiol Heart Circ Physiol, 295: H482-H490, 2008.

Laslett, "Normal left main coronary artery diameter can be predicted from diameters of its branch vessels," Clinical Cardiology 18 (10): 580-582, 1995.

Ofili et al., "Differential characterization of blood flow, velocity, and vascular resistance between proximal and distal normal epicardial human coronary arteries: analysis by intracoronary Doppler spectral flow velocity," Am Heart J. 130:1 37-46, 1995.

Ohta et al., "Rheological Changes After Stenting of a Cerebral Aneurysm: A Finite Element Modeling Approach," Cardiovascular and Interventional Radiology (2005) 28:768-772.

Pijls et al., "Fractional Flow Reserve (FFR) Post-Stent Registry Investigators" Coronary pressure measurement after stenting predicts adverse events at follow-up: a multicenter registry, Circulation 2002; 105:2950-2954.

Seiler et al., "Basic structure-function relations of the epicardial coronary vascular tree, Basis of quantitative coronary arteriography for diffuse coronary artery disease," Circulation 85 (6): 1987-2003, 1992.

Siebes et al., "Single-wire pressure and flow velocity measurement to quantify coronary stenosis hemodynamics and effects of percutaneous interventions," Circulation 109:756-762, 2004.

Sihan et al., "A Novel Approach to Quantitative Analysis of Intravascular Optical Coherence Tomography Imaging," Computers in Cardiology 2008; 35:1089-1092.

Sihan et al., "Fully Automatic Three-Dimensional Quantitative Analysis of Intracoronary Optical Coherence Tomography: Method and Validation," Catheterization and Cardiovascular Interventions 74:1058-1065 (2009).

Spaan, "Coronary Blood Flow," Ch 12. Dordrecht, the Netherlands: Kluwer Acedemic Publishers, Boston; 1991: pp. 333-361.

Takagi et al., "Clinical potential of intravascular ultrasound for physiological assessment of coronary stenosis," Circulation 100: 250-255, 1999.

Verhoeff et al., "Influence of percutaneous coronary intervention on coronary microvascular resistance index," Circulation 111:76-82, 2005.

White et al., "Does visual interpretation of the coronary angiogram predict the physiologic importance of coronary stenoses?," N. Engl J Med 310:13 819-824, 1984.

Wilson et al., "Prediction of the physiologic significance of coronary arterial lesions by quantitative lesion geometry in patients with limited coronary artery disease," Circulation 75: 723-732, 1987.

Perez-Rovira et al., "Deformable Registration of Retinal Fluorescein Angiogram Sequences Using Vasculature Structures", 32nd Annual Conf. of IEEE EMBS, 2010, pp. 4383-4386.

Herrington et al., "Semi-automated boundary detection for intravascular ultrasound," Computers in Cardiology 1992 Proceedings., pp. 103-106, Oct. 1992.

Sonka et al., "Segmentation of intravascular ultrasound images: a knowledge-based approach," IEEE Transactions on Medical Imaging, 14(4):719-732, Dec. 1995.

Mojsilovic et al., "Automatic segmentation of intravascular ultrasound images: A texture-based approach," Annals of Biomedical Engineering, 25:1059-1071, Nov. 1997.

Gil et al., "Automatic segmentation of artery wall in coronary IVUS images: a probabilistic approach," Computers in Cardiology 2000; 27:687-690.

Haas et al., "Segmentation of 3D intravascular ultrasonic images based on a random field model," Ultrasound in Medicine & Biology, 26:2, 297-306, 2000.

Kovalski et al., "Three-dimensional automatic quantitative analysis of intravascular ultrasound images," Ultrasound in Medicine & Biology, 26(4):527-537, 2000.

Pujol et al., "Intravascular Ultrasound Images Vessel Characterization using AdaBoost," Functional Imaging and Modeling of the Heart: Lecture Notes in Computer Science, pp. 242-251, 2003.

Taki et al., "Automatic segmentation of calcified plaques and vessel borders in IVUS images," International Journal of Computer Assisted Radiology and Surgery, 3(3-4):347-354, Sep. 2008.

van den Berg et al., "Using three-dimensional rotational angiography for sizing of covered stents," Am. J. Roentgenology, 178:149-152 (2002).

Wong et al., "A novel method of coronary stent sizing using intravascular ultrasound: safety and clinical outcomes," Int. J. Anglol. , 18(1): 22-24 2009.

Bonnema et al., "An automatic algorithm for detecting stent endothelialization from volumetric optical coherence tomography datasets", Physics in Medicine and Biology, 53 :12, Jun. 21, 2008, pp. 3083-3098.

Unal et al., "Stent implant follow-up in intravascular optical coherence tomography images," Int J Cardiovasc Imaging, DOI 10.1007/s10554-009-9508-4, published online Sep. 24, 2009, 8 pgs.

Xu et al., "Characterization of atherosclerosis plaques by measuring both backscattering and attenuation coefficients in optical coherence tomography," Journal of Biomedical Optics, 13:3, May/Jun. 2008, 8 pgs.

Takano et al.. "Evaluation by Optical Coherence Tomography of Neointimal Coverage of Sirolimus-Eluting Stent Three Months After Implantation," American Journal of Cardiology, vol. 99, No. 8, Apr. 14, 2007, pp. 1033-1038.

Tung et al., "Automatic Detection of Coronary Stent Struts in Intravascular OCT Imaging," Proceedings of SPIE, vol. 8315, Feb. 22, 2012 (8 pgs.).

Shengxian Tu et al., "In vivo comparison of arterial lumen dimensions assessed by co-registered three-dimensional (3D) quantitative coronary angiography, intravascular ultrasound and optical coherence tomography", Int. J. Cardiovasc Imaging (2012) 28:1315-1327.

Palti-Wasserman et al., "Identifying and Tracking a Guide Wire in the Coronary Arteries During Angioplasty from X-Ray Images", IEEE transactions on biomedical engineering, 44:2, Feb. 1997, pp. 152-164.

Dave Fornell, "The Advantages and Disadvantages of OCT vs. IVUS", Diagnostic and Interventional Cardiology, May 18, 2011, pp. 1-4.

(56) References Cited

OTHER PUBLICATIONS

International Search Report and Written Opinion of the International Searching Authority for International Application No. PCT/US2016/062161 mailed from the International Searching Authority dated Feb. 24, 2017 (16 pages).

* cited by examiner

INTRAVASCULAR IMAGING AND GUIDE CATHETER DETECTION METHODS AND SYSTEMS

CROSS-REFERENCE TO RELATED APPLICATIONS

This application claims priority to U.S. Provisional Patent Application No. 62/257,662 filed on Nov. 19, 2015, the disclosure of which is herein incorporated by reference in their entirety.

FIELD

In part, the disclosure relates generally to intravascular measurements, the calibration and configuration thereof, and related diagnostic methods and devices.

BACKGROUND

Coronary artery disease is one of the leading causes of death worldwide. The ability to better diagnose, monitor, and treat coronary artery diseases can be of life saving importance. Intravascular optical coherence tomography (OCT) is a catheter-based imaging modality that uses light to peer into coronary artery walls and generate images thereof for study. Utilizing coherent light, interferometry, and micro-optics, OCT can provide video-rate in-vivo tomography within a diseased vessel with micrometer level resolution.

Viewing subsurface structures with high resolution using fiber-optic probes makes OCT especially useful for minimally invasive imaging of internal tissues and organs. This level of detail made possible with OCT allows a clinician to diagnose as well as monitor the progression of coronary artery disease. OCT images provide high-resolution visualization of coronary artery morphology and can be used alone or in combination with other information such as angiography data and other sources of subject data to aid in diagnosis and planning such as stent delivery planning Imaging of portions of a patient's body provides a useful diagnostic tool for doctors and others. OCT, ultrasound and other data collection modalities use guide catheters to position a probe in a blood vessel prior to collecting data. In many circumstances, collecting data when a data collection probe is within the guide catheter is undesirable. Accordingly, a need therefore exists to detect the location of a guide catheter. The present disclosure addresses this need and others.

SUMMARY

In part, the disclosure relates to a method of method of a detecting a guide catheter disposed in a lumen of a blood vessel. The method includes collecting a set of intravascular data using a probe disposed in the blood vessel and positioned using the guide catheter; determining an intensity value for a plurality of sets of intravascular data; and identifying a subset of the intravascular data as containing the guide catheter based upon the intensity value of the subset being greater than the intensity value of the other sets of intravascular data.

In one embodiment, the intensity value is an average intensity value determined on a per scan line basis. In one embodiment, the method includes identifying intravascular data that includes the guide catheter and excluding such intravascular data when performing stent detection. In one embodiment, the method includes identifying intravascular data that includes the guide catheter and excluding such intravascular data when performing shadow detection. In one embodiment, the intravascular data comprises a plurality of frames.

In one embodiment, the intravascular data comprises a plurality of scan lines. In part, the disclosure relates to a method of a detecting a guide catheter disposed in a lumen of a blood vessel. The method includes consecutively collecting a first set of intravascular data and a second set of intravascular data using an intravascular imaging probe, the second set comprises guide catheter image data; on a per frame basis performing a circle fit to determine a per frame diameter value; identifying a deviation in one or more per frame values as corresponding to a frame that includes guide catheter image data; and excluding frames that include guide catheter image data from an intravascular data processing module. In one embodiment, the method includes detecting a peak or relative extrema to validate an indication of guide catheter image data being present.

In one embodiment, the intravascular data processing module is a stent detection module. In one embodiment, the intravascular data processing module is a side branch detection module. In one embodiment, each frame is data that corresponds to a cross-section perpendicular to the motion of the pullback of a probe through a blood vessel In part, the disclosure relates to a method of a detecting a guide catheter disposed in a lumen of a blood vessel. The method includes collecting data in the blood vessel as a plurality of scan lines by optical coherence tomography; storing the collected data in a memory in communication with a processor; storing, in one or more memory devices, a plurality of measured diameter values on a per frame basis; detecting a deviation in diameter values from adjacent frames; and identifying the frame having the higher frame number as a guide catheter containing frame.

In one embodiment, the method includes excluding the guide catheter containing frame when performing stent detection. In one embodiment, the method includes excluding the guide catheter containing frame when performing side branch detection. In one embodiment, the method includes excluding the guide catheter containing frame when displaying information from an intravascular pullback on a display. In one embodiment, the method includes generating a plurality of frames using the plurality of scan lines. In one embodiment, each frame is data that corresponds to a cross-section perpendicular to the motion of the pullback of a probe through a blood vessel.

In part, the disclosure relates to computer-based methods, systems and devices suitable to detect a guide catheter and flag or exclude frames or other image data associated therewith from use by other intravascular processing stages or modules. The guide catheter can also be a delivery catheter and vice versa. The disclosure relates to identifying the guide catheter that positions an intravascular imaging probe such as an imaging catheter. The geometry of the guide catheter, intensity variations thereof, and signal transitions associated with geometric properties and measurements of the blood vessel and the guide catheter are used to identify frames corresponding to guide catheter in one or more intravascular data sets. In one embodiment, the intensity variations can be maximums, minimums, relative extremums and other curve or plot transition points such as points of increasing or decreasing slope.

In one embodiment, the method further includes executing an image data processing pipeline, using one or more computing devices, the image data processing pipeline comprising a lumen detection image data processing module, a guide catheter detection module, a stent detection software module and a side branch detection software module. In one embodiment, one or more downstream modules in the image data processing pipeline receive intravascular data with respect to which the identified guide catheter containing frames or scan lines are removed or otherwise excluded from processing by the one or more downstream modules.

In one embodiment, guide catheter detection frames are identified and flagged such that they are ignored by subsequent intravascular image data processing stages such a stent detection software module and/or a side-branch software module. In one embodiment, guide catheter detection frames are identified and removed from the intravascular image data prior to transmitting or making such data available to subsequent intravascular image data processing stages such a stent detection software module and/or a side-branch detection software module.

In one embodiment, one or more steps can be performed automatically or without user input other than an initial user input. For example, such a user input can be to navigate relative to one or more images, enter information, select or interact with an input such as a controller or user interface component, indicate one or more system outputs or otherwise interact with an intravascular probe or a data collection system in communication therewith. Notwithstanding the foregoing, the scope of the terms discussed herein is not intended to be limiting, but rather to clarify their usage and incorporate the broadest meaning of the terms as known to those of ordinary skill in the art.

In one embodiment, the guide catheter (GC) has an average brightness on a given frame that is brighter than a given tissue frame. As a result, this brightness or an average brightness for each frame can be used to distinguish lumen only frames from GC containing frames. In plots of intensity or diameters versus frame number the more consistent values can correspond to the consistent circular diameter of the GC and be used as an identifying signature. A sharp drop or transition in the intensity versus frame number (moving from proximal to distal) can indicate the frame that identifies the tip of the GC. In one embodiment, a circle fit method is used as a secondary method to validate the output of an intensity based GC detection method such as a max intensity method.

In one embodiment, the GC detection method measures chords in the image data on a per frame basis. The chords pass from one point on the lumen, through the image center, to the lumen on the opposite side. The chords can be plotted as a histogram. The dominant chord value can be selected as an approximation of the diameter of the lumen for a given frame. An abrupt change in diameter, when scanning frames from proximal to distal, can indicate the tip of the catheter.

In one embodiment, the GC detection software module and associate method process one frame at a time and determines best fit circles and/or diameter values. In one embodiment, one diameter is determined per frame—starting at proximal end (or distal end). The method evaluates each diameter and if it is within an acceptable deviation level indicative of consistent diameters continue to the next frame. Upon the detection of a change in diameter outside of the acceptable level, the software can treat that frame as having a diameter exceeding that of the GC and corresponding to a frame of lumen only data. In one exemplary embodiment, a frame is data that corresponds to a cross-section perpendicular to the motion of the pullback of a probe through a blood vessel.

In part, the disclosure relates to a method of method of a detecting a guide catheter disposed in a lumen of a blood vessel. The method includes collecting a set of intravascular data using a probe disposed in the blood vessel and positioned using the guide catheter; determining an intensity value for a plurality of sets of intravascular data; and identifying a subset of the intravascular data as containing the guide catheter based upon the intensity value of the subset being greater than the intensity value of the other sets of intravascular data.

In one embodiment, the intensity value is an average intensity value determined on a per scan line basis. In one embodiment, the method includes identifying intravascular data that includes the guide catheter and excluding such intravascular data when performing stent detection. In one embodiment, the method includes identifying intravascular data that includes the guide catheter and excluding such intravascular data when performing shadow detection. In one embodiment, the intravascular data comprises a plurality of frames.

In one embodiment, the intravascular data comprises a plurality of scan lines. In part, the disclosure relates to a method of a detecting a guide catheter disposed in a lumen of a blood vessel. The method includes consecutively collecting a first set of intravascular data and a second set of intravascular data using an intravascular imaging probe, the second set comprises guide catheter image data; on a per frame basis performing a circle fit to determine a per frame diameter value; identifying a deviation in one or more per frame values as corresponding to a frame that includes guide catheter image data; and excluding frames that include guide catheter image data from an intravascular data processing module.

In one embodiment, the method includes detecting a peak or relative extrema to validate an indication of guide catheter image data being present. In one embodiment, the intravascular data processing module is a stent detection module. In one embodiment, the intravascular data processing module is a side branch detection module. In one embodiment, each frame is data that corresponds to a cross-section perpendicular to the motion of the pullback of a probe through a blood vessel In part, the disclosure relates to a method of a detecting a guide catheter disposed in a lumen of a blood vessel. The method includes collecting data in the blood vessel as a plurality of scan lines by optical coherence tomography; storing the collected data in a memory in communication with a processor; storing, in one or more memory devices, a plurality of measured diameter values on a per frame basis; detecting a deviation in diameter values from adjacent frames; and identifying the frame having the higher frame number as a guide catheter containing frame.

In one embodiment, the method includes excluding the guide catheter containing frame when performing stent detection. In one embodiment, the method includes excluding the guide catheter containing frame when performing side branch detection. In one embodiment, the method includes excluding the guide catheter containing frame when displaying information from an intravascular pullback on a display. In one embodiment, the method includes generating a plurality of frames using the plurality of scan lines. In one embodiment, each frame is data that corresponds to a cross-section perpendicular to the motion of the pullback of a probe through a blood vessel.

BRIEF DESCRIPTION OF DRAWINGS

The figures are not necessarily to scale, emphasis instead generally being placed upon illustrative principles. The figures are to be considered illustrative in all aspects and are not intended to limit the disclosure, the scope of which is defined only by the claims.

DETAILED DESCRIPTION

Figure 1A:
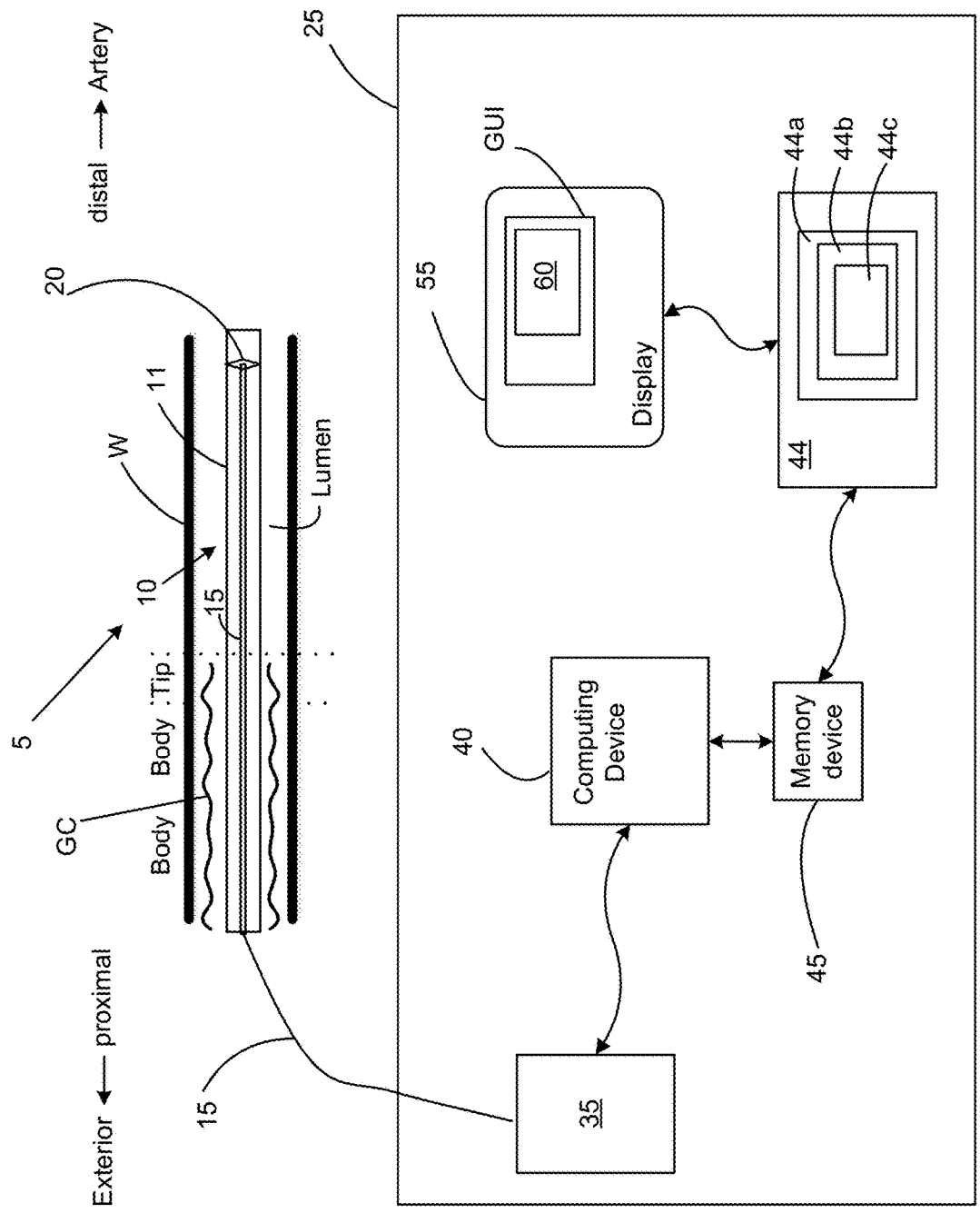
FIG. 1A is a schematic diagram of a data collection system and a data collection probe positioned in a guide catheter disposed in the lumen of a blood vessel in accordance with an illustrative embodiment of the disclosure.

In part, the disclosure relates to intravascular data collection and imaging. An exemplary system 5 suitable for collecting signals from a blood vessel 10 such as an artery having a vessel wall 12 and a lumen is shown in FIG. 1A. Intravascular probes can be positioned in a lumen of blood vessel by a catheter, such as a guide or a delivery catheter. These probes can obtain distance measurements relative to a sample such as, for example, a blood vessel or objects disposed therein. The probes can include rotatable elements that direct light or ultrasound in an artery as after the probe has been delivered by a catheter after which the probes are pulled back through the artery to generate a set of image data. Optical coherence tomography (OCT) is an imaging modality that uses an interferometer to obtain such data. Similarly, intravascular ultrasound or IVUS uses sound waves to generate intravascular image data. One intravascular data has been collected relative to a blood vessel the data can be played back as a series of frames, cross-sectional views, longitudinal views, and other parameters generated by the measurements obtained from the blood vessel such as lumen diameters, side branch locations, and various other measured or detected features and information of interest.

The disclosure relates to guide catheter detection in OCT data playback wherein the OCT imaging catheter, if fed through a guide catheter and extended beyond the area of interest, will in some cases, allow the pullback to continue partially into the guide catheter, making it useful to identify the guide catheter in the pullback. See FIGS. 1A and 1B for different positions of probe and imaging catheter.

The intravascular data collection probe, such as an OCT or IVUS or combination probe, can be implemented using an imaging catheter that includes one or more rotatable optical or acoustic transceivers at probe tip 20 as shown in FIG. 1A or other probe positions. The imaging catheter or probe is fed through a guide or delivery catheter and extended beyond an area of interest from which a pullback through the lumen of the vessel will be performed. In some scenarios, the pullback can continue partially into the guide catheter and the intravascular image data collected can include a section of the guide catheter and associated scan lines or frames therein. Images, other detection routines, and other parts of an intravascular data processing pipeline can then include such guide catheter frames or scan lines of data.

Using the image data from inside the guide catheter does not have any clinical applications at this time. Further, the use of guide catheter data may provide false positive results or cause other triggering or operational problems in the various other detection algorithms and methods in the data processing pipeline. For example, including the frames or scan lines of guide catheter data may cause errors or other problems with stent detection, side-branch detection, or other processing modules that relay on the intravascular data from the pullback as an input. As a result, identifying the guide or delivery catheter in the intravascular data obtained during a pullback through a lumen of a blood vessel is advantageous in order that such data can be flagged or otherwise excluded to prevent other errors or unwanted effects in the software-based intravascular data processing modules.

Figure 1B:
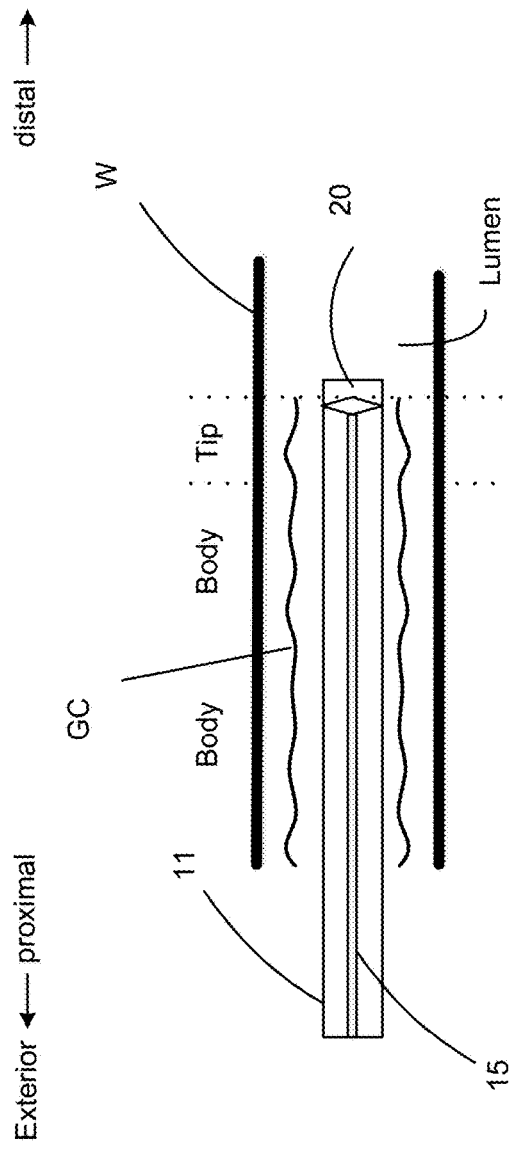
FIG. 1B is a schematic diagram of a data collection probe disposed in and imaging through a guide catheter disposed in the lumen of a blood vessel in accordance with an illustrative embodiment of the disclosure.

As shown in FIG. 1A, a blood vessel 5 can be imaged using a data collection probe 10. The blood vessel has an associated vessel wall W and a lumen that the wall borders. The data collection probe 10 can include an imaging catheter 11 and an optical fiber 15. In addition, the optical fiber 15 is in optical communication with a probe tip 20. The probe 10 can be introduced and pulled back along a length of a blood vessel 5 while collecting data. The probe is introduced or delivered at a desired location in the vessel 5 using a guide catheter GC. The probe typically is introduced through an artery such that it enters the subject and move in a distal direction. As shown in FIG. 1B, which shows a zoomed in view of the GC and probe 10, the imaging catheter 11 and probe 10 pulls back within the GC and can image through the wall of the GC. Detecting the GC in the resultant images is desirable because the GC can include structures that generate shadows which can cause it to appear as a stent or otherwise be misinterpreted by software imaging processing modules such as a stent detection or shadow detection software module.

The probe 10 including the imaging catheter 11 extends along the body of the guide catheter GC and the tip of the guide catheter as shown. The vertical dotted lines show the delineation between the tip and body sections of the guide catheter GC. As the imaging catheter 11 is retracted (pulled-back) along the length of the vessel, a plurality of scans or OCT data sets are collected as the probe or a portion thereof rotates. This is referred to as a pullback in one embodiment. During a pullback the probe moves in the proximal direction. These data sets can be used to identify blood vessel characteristics such as lumen area and diameter, image the vessel, and identify catheters disposed in the vessel as described herein. Although an optical fiber 15 is shown, the probe 10 can be an ultrasound probe such as an IVUS probes or other data collection probes. The images generated and subsequent image processing to detect blood vessel features can have errors and artifacts introduced in them if frames containing the guide catheter are treated as images of the blood vessel. As a result, frames that include that guide catheter are identified in one embodiment. In one embodiment, the display of the guide catheter is included as part of the information displayed with regard to the image frames of the pullback. In one embodiment, once the guide catheter is identified it is excluded from subsequent image processing and/or display in one embodiment.

Figure 2A:
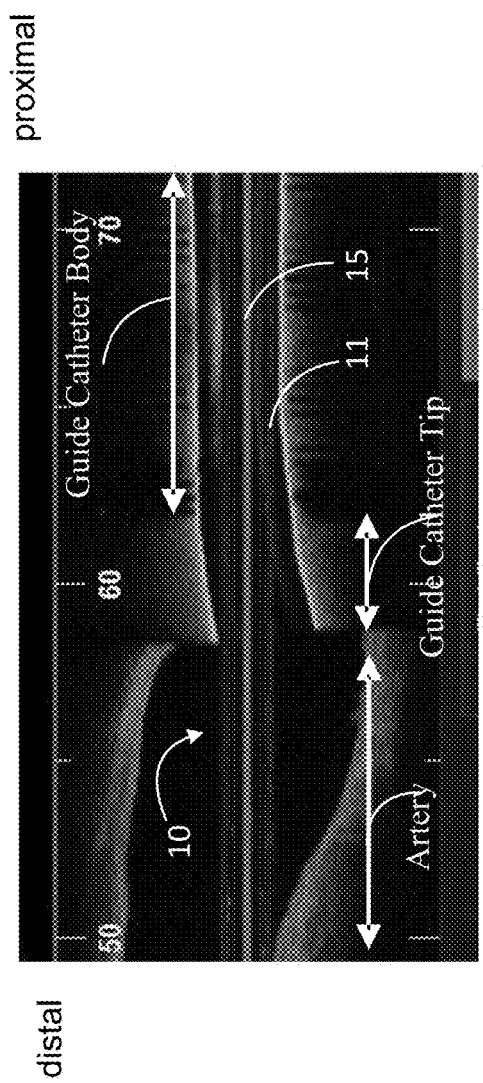
FIG. 2A is a longitudinal view of a guide catheter disposed in the lumen of a blood vessel and an imaging catheter spanning the distal and proximal sides of the image in accordance with an illustrative embodiment of the disclosure.

In one embodiment, the data collection probe 10 connects such as via a releasable coupler with an intravascular data collection system 25 that includes an interferometer and a data processing system. In one embodiment, the probe is an OCT probe and the system 25 is OCT system or a multi-modal system that includes other data collection modalities. The probe tip 20 includes a beam director in one embodiment. The distance measurements collected using the probe 10 can be processed to generate frames of image data such as cross-sectional views or longitudinal views (L-mode views) of the blood vessel. FIG. 2A shows such a view of a blood vessel and guide catheter having a body and a tip portion and an intravascular probe 10. When the guide catheter ends at its tip, the artery continues with the probe 10 in the lumen. The probe 10 has an imaging catheter 11 and an optical fiber 15. For clarity, a cross-sectional view can include without limitation a longitudinal view. These images can be processed using one or more image data processing modules or stages such as outlined herein.

For a blood vessel 5 as shown in FIG. 1A, which includes a guide or delivery catheter GC disposed in the lumen of the blood vessel various types of data collection probes and related systems 25 can be used. A releasable probe interface device 35 can be use to connect to probe 10. In one embodiment, the system 25 includes a processor, memory, or other components configured to execute various data processing stages or modules. These stages or modules operate upon and transform image data. These modules or stages can include a lumen detection software module and stage, a guide or delivery catheter detection software module and stage, and various other stages. The memory includes a first and second memory and may include a plurality of memory elements. These memory elements can store intravascular data collected using the probe and various transformations thereof such as, without limitation, data relating to a detected lumen boundary, detected struts, and detected GC frames or scan lines.

FIG. 1A is a high level schematic diagram depicting a data collection probe and an OCT data collection system 25. When the system 25, is an OCT system it can include a suitable light source that satisfies the coherence and bandwidth requirements of the applications and data collection described herein. As shown, the guide catheter GC is introduced into the lumen such as an arterial lumen and the probe 10 including an imaging catheter is disposed in the guide catheter GC and also spans the lumen and extends beyond the guide catheter GC. The probe and imaging catheter also move within the GC at the end of the pullback in one embodiment such as shown in FIG. 1B. The probe 10 can include a rotating or slidable fiber 15 that directs light forward into the lumen or at a direction angled relative to the longitudinal axis of the fiber 15. As a result, in the case of light that is directed from the side of the probe as the fiber 15 rotates, OCT data is collected with respect to the walls W of the blood vessel 5. The walls W of the blood vessel 5 define a lumen boundary. This lumen boundary can be detected using the distance measurements obtained from the optical signals collected at the probe tip 20 using lumen detection software component. If stents are disposed in the blood vessel they can also be detected using a shadow detection software component.

Figure 2B:
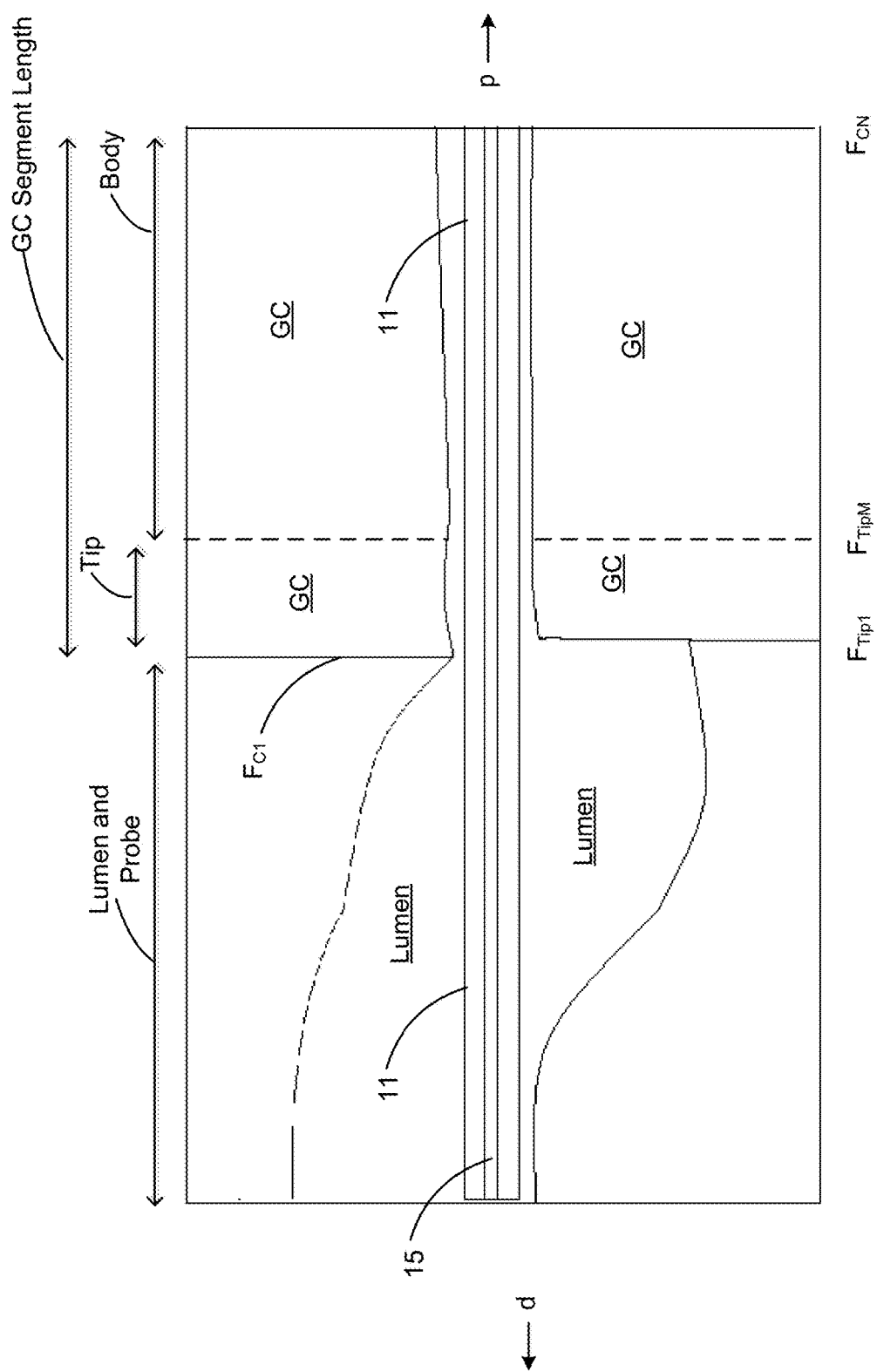
FIG. 2B is a schematic diagram of data collection system and a data collection probe in accordance with an illustrative embodiment of the disclosure.

As shown in FIG. 1A, the probe tip 20 is positioned in the lumen such that it is distal to guide catheter GC disposed in the blood vessel 5. The body and tip of the GC are labeled and bounded by the vertical dotted lines. The right-most vertical dotted line marks the guide catheter tip, and that the left-most dotted line marks the start of the body of the guide catheter. Additional details relating to the position and views of an exemplary guide catheter are shown in FIGS. 2A and 2B. The probe tip 20 is configured to transmit light and receive backscattered light from objects, such as stents, blood and the wall W of the blood vessel 5. The right side of FIG. 2A includes the GC body and tip. These portions of the right side have an image intensity level that is greater than the intensity level on the left side. In addition, the left side of FIG. 2A shows the expansion of the lumen relative to the diameter of the GC. This variation in intensity level between lumen and GC containing frames and the expanded diameter of the lumen image frames as a transition from a GC containing frame can be used to detect the GC in one embodiment.

In one embodiment, an optical receiver 31 such as a balanced photodiode based system can receive light exiting the probe 10. A computing device 40 such as a computer, processor, ASIC or other device can be part of the OCT system 10 or can be included as a separate subsystem in electrical or optical communication with the OCT system 10. The computing device 40 can include memory, storage, buses and other components suitable for processing data and software 44 such as image data processing stages configured for lumen detection, guide catheter detection, side branch detection, and pullback data collection as discussed below.

Figure 3:
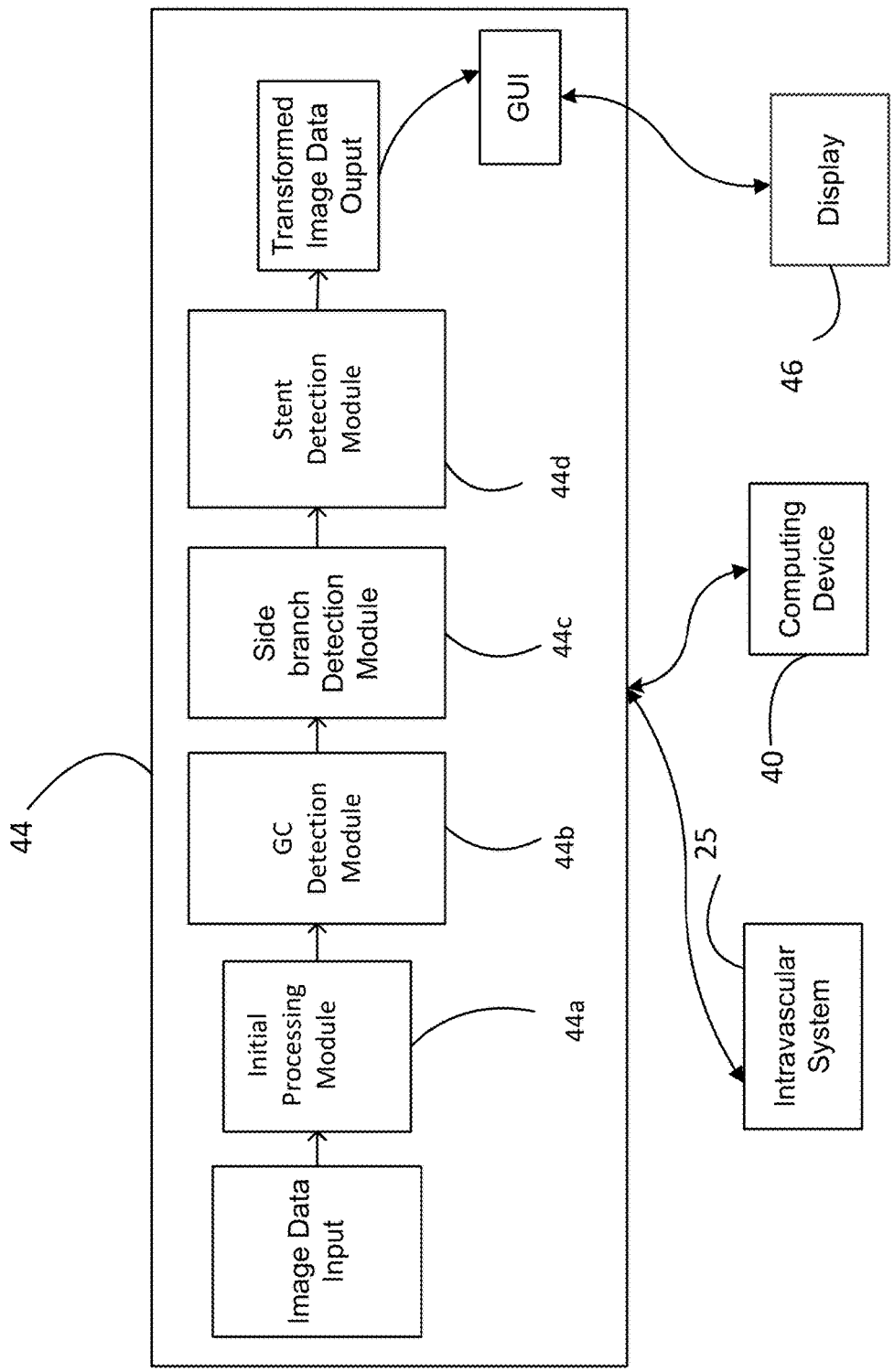
FIG. 3 is a schematic diagram of an image data processing pipeline that includes a guide catheter detection module in accordance with an illustrative embodiment of the disclosure.

In one embodiment, the computing device 40 includes or accesses intravascular data transforming and processing software modules or programs 44. These software programs or modules can be a sequenced pipeline of image data processing and feature detection modules include a plurality of software modules shown without limitation to three modules as exemplary software modules 44a, 44b, and 44c. The software modules can include for example a lumen detection module, a stent detection module, and a side branch detection module. In one embodiment, GC detection is performed prior to stent and side branch detection. The software modules or programs 44 can include an image data processing pipeline or component modules thereof and one or more graphical user interfaces (GUI). An exemplary image processing pipeline 50 for transforming collected OCT data into two dimensional and three dimensional views of blood vessels and stents is depicted in FIG. 3. The image data processing pipeline or any of the methods described herein are stored in memory and executed using one or more computing devices such as a processor, device, or other integrated circuit.

As shown, in FIG. 1A, a display 55 can also be part of the system 10 for showing information 60 such as cross-sectional and longitudinal views of a blood vessel generated using collected OCT data. FIG. 2B is an example of a display of such information 60. In part, the disclosure relates to detecting the guide catheter GC such that pullback data generated as a result of the probe 10 moving back into the GC at the end of a pullback is not useful for display to a clinician and if included can cause errors in software pipeline modules 44c and 44d including as shown in FIG. 3. This OCT-based information 47 can be displayed using one or more graphic user interface(s) (GUI). In addition, this information 47 can include, without limitation, shadow regions, stents, and a lumen border. The computing device 40 can also include software or programs 44, which can be stored in one or more memory devices 45, configured to identify frames and/or scan lines that include guide catheter GC information such as shown in FIGS. 1B, 2A and 2B in which GC data is part of the pullback data set and other software image data processing pipeline modules as shown in FIG. 3.

Once the OCT data is obtained with a probe and stored in memory; it can be processed to generate information 47 such as a cross-sectional, a longitudinal, and/or a three-dimensional view of the blood vessel along the length of the pullback region or a subset thereof. These views can be depicted as part of a user interface.

As shown, in FIG. 3, a sequence of a plurality of image processing software modules including an initial processing module 44a which can include a lumen detection software module and a guide catheter detection module 44b are executing on one or more processors. These modules include instructions to operate automatically or in response to a user selection or action on intravascular image data including scan line or polar data. If the initial processing module includes a lumen detection module the module can process the data using to determine a lumen boundary and identify one more points on the boundary. In one embodiment, the lumen detection module provides a lumen boundary as an input to the GC detection module 44b. The GC detection module 44b can detect a frame or a position of a guide catheter disposed in the lumen relative to the lumen boundary using geometric properties of the catheter, material properties of the catheter such as intensity behavior or other optical signatures, and combinations thereof.

In one embodiment, as data is collected using a probe positioned in a lumen using a delivery or guide catheter data is acquired one scan line at a time and stored in memory in communication with one or more computing devices. A scan line includes image or depth data along a radial line. A sequence of samples along a ray originating at the catheter center to the maximum imaging depth is referred to as a scan line. Thus, a given scan line can include a portion of the guide catheter and identified as a point or frame or scan line or a set thereof that includes the start of the guide catheter in the vessel or are otherwise within the guide catheter. These points or sets of guide catheter containing intravascular data can then be excluded from subsequent steps in the image data processing pipeline 44. Thus, the shadow detection module 44c and/or the stent detection module 44d can operate on scan lines or other image data representations with the GC image data excluded. This reduces stent and shadow detection errors which could occur if modules 44c and 44d operated upon GC containing image data.

Guide Catheter Detection

As discussed above, the guide catheter (GC) is the catheter through which the imaging catheter or intravascular imaging probe is delivered to the coronary arteries. As a result, guide catheters are also sometimes referred to as delivery catheters. GCs can be of various configurations and thus can have different imaging signatures. Some GCs include braided components or other structures that result in shadows when an imaging probe is disposed in and images through a GC. In part, the disclosure relates to a guide catheter detection (GCD) module and associated methods that can be used alone or as part of an intravascular image data processing pipeline. The GCD module detects the presence of the guide catheter at the proximal end of a pullback.

In one embodiment the GCD module determines the first frame, the first scan line, a range of frames, or a range of scan lines in which the guide catheter appears. This set of pullback data with GC detections can then be excluded from display to a user and from processing using stent detection, shadow detection, or other detection modules that may generate erroneous results if the GC detections were included and processed using such modules.

For some guide catheter designs, the catheter includes a braid such as a metal braid. The metal braid and other optical properties of the guide catheter allow its appearance in an OCT or other intravascularly acquired data set acquisition to be detected with some of the methods described herein. In one embodiment, the bright reflective surface and the appearance of many shadows distributed about the 2-D acquired image of the guide catheter is used as a signature or a set or characteristics to facilitate its detection using the computer-based methods described herein. Because the guide catheter portion of the pullback is of no clinical relevance it is useful to identify frames contained in the guide catheter so that downstream modules can remove them from consideration at their discretion.

As described herein, FIG. 2A shows an exemplary longitudinal view of an image of an artery generated using image data from a pullback through the artery. A cross-sectional image can be formed using an intravascular data collection system such as an OCT, IVUS, or other suitable system by arranging the collection of scan lines to form longitudinal, cross-sectional and other views. An example of such a view is shown in FIG. 2A which shows a lumen cross-section with a guide catheter. FIG. 2B shows a schematic representation of a similar view. The guide catheter is shown on the right or proximal side of the image. The lumen without the guide catheter and the imaging catheter or intravascular data collection probe is shown on the left or the distal side of the figure. In FIG. 2B, $F_{C1}$ is the first GC frame and $F_{tip1}$ is a first frame with the tip of the GC. $F_{tipM}$ is the last fame of the GC tip. $F_{CN}$ is the last GC frame.

The catheter body and the catheter tip have different profiles as can be shown from the longitudinal view of FIG. 2A. The longitudinal view is a representation of a slice along the length of a vessel segment. A series of cross-sectional frames or scan line representations, but as the picture illustrates there may be a difference in character between the two. The GC segment length is shown and includes the tip and remaining portion of the GC.

In one embodiment, guide catheter detection is independent of size and shape of the catheter. In one embodiment, one or more guide catheter detection processes are executed using one or more computing devices. The detection of the guide catheter is independent of the size and manufacturer/model of the catheter. In one embodiment, 2, 3, 4 or N, wherein N is greater than four detection processes or algorithms can be used. In one embodiment, the detection processes or algorithms are independent of each other such that one such process or algorithm is not an input to or required to run one or more of the other detection processes or algorithms. The final determination of the presence and location of the catheter is derived by using a combination of the independent algorithm results in one embodiment.

In one embodiment, the disclosure models the GC as having a substantially circular cross-section. As a result, the cross-section of the GC should be substantially the same along its length until the tip region is reached. In addition, frames of image data that do not include the guide catheter will also exhibit a change in diameter that deviates from the substantially circular cross-section and consistent diameter measurements of the guidewire. These processes can be executed serially or in parallel.

In one embodiment, the processes or methods of detecting a guide catheter in a lumen of a subject include one or more of the following detection processes/algorithms: average-max intensity, circle-fit, chord-histogram, circle-histogram, and combinations of the foregoing or their respective steps. In one embodiment, a given detection method is based on one or more of the material properties of guide catheter, optical signature of guide catheter, ultrasound signature of guide catheter, geometry of catheter, consistent circular geometry of guide catheter and the associated consistent radii, diameters, and chords thereof, and intensity profiles of scan lines that are brighter relative to that of the lumen. In one embodiment, a first detection method is used to identify one or more frames that include a guide catheter and a second detection method is used if the output of the first detection method is indeterminate.

Average-Max Intensity Detection Method

In one embodiment, the average-max intensity detection method is based on one or more material property of the catheter. Other intensity values can be used in a given embodiment. The material from which the catheter is made has an intensity profile or signature that will differ from that of the tissue surrounding it and the lumen of the blood vessel in which it is disposed. The average-max intensity detection method identifies the tip of a catheter as the point or a range of points at which the average intensity of the image undergoes a transition such as a drop, slope change, spike, or other identifiable intensity transition. In one embodiment, the transition is a sharp increase. In one embodiment, the transition is a sharp increase followed by a sharp decrease such as spike or other transition.

Average-Max Intensity Method

For each frame the maximum intensity is identified on each scan line. A scan line represents intensity values at varying distances radially from the imaging sensor. The average of these maximum intensities across all scan lines is computed and stored for each frame. After all frames have been scored the resulting data is examined. The algorithm looks for a sharp drop of intensity when scanning from the proximal end. The figures discussed below show three cases with the proximal end on the right. The plots of various measured or otherwise determined parameters obtained using the data generated as a result of pullback the imaging catheter or probe through the artery indicate three different outcomes.

Figure 4:
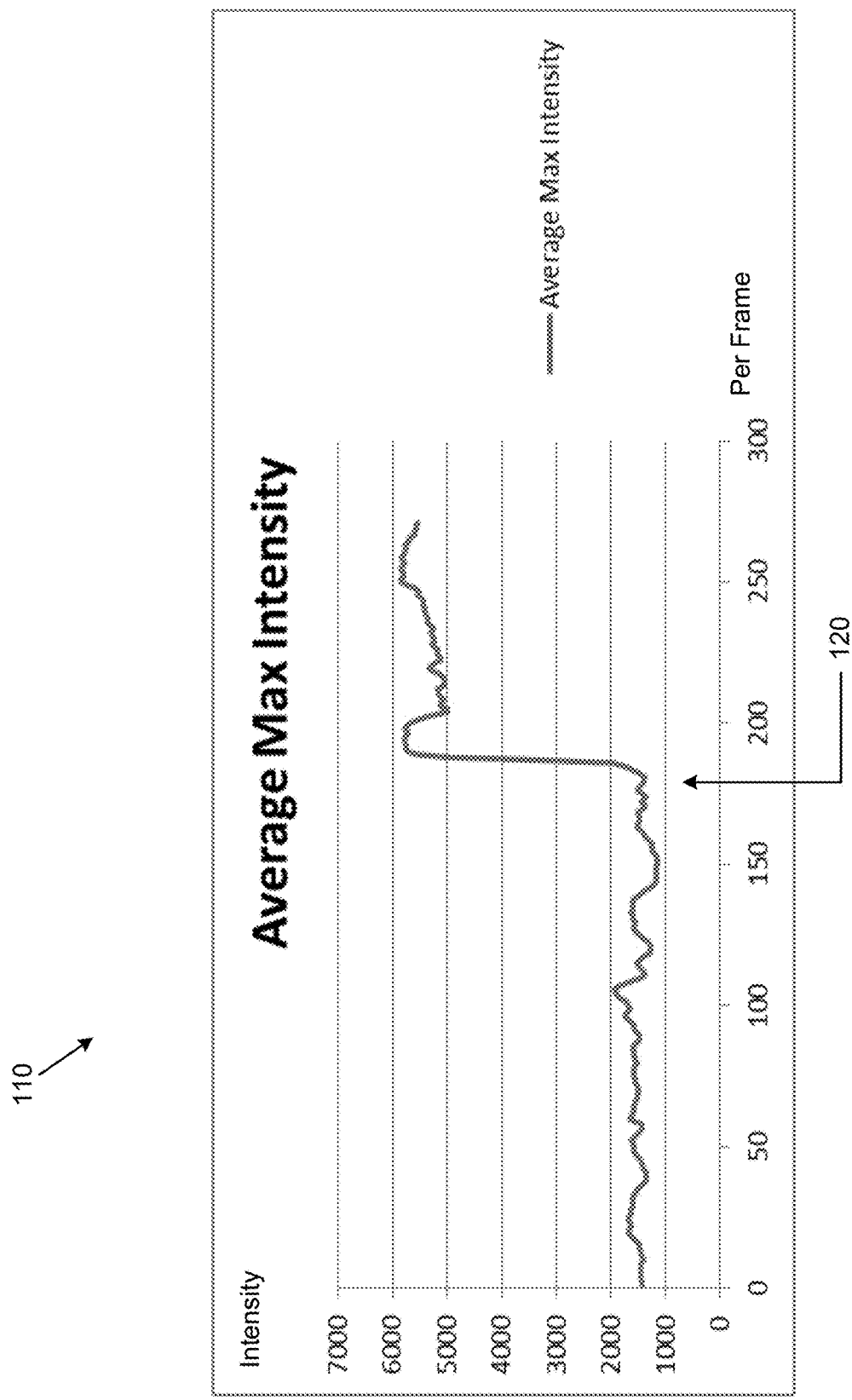
FIG. 4 is a plot of average maximum intensity per frame in which a positive identification of the guide catheter has been achieved in accordance with an illustrative embodiment of the disclosure.
Figure 6:
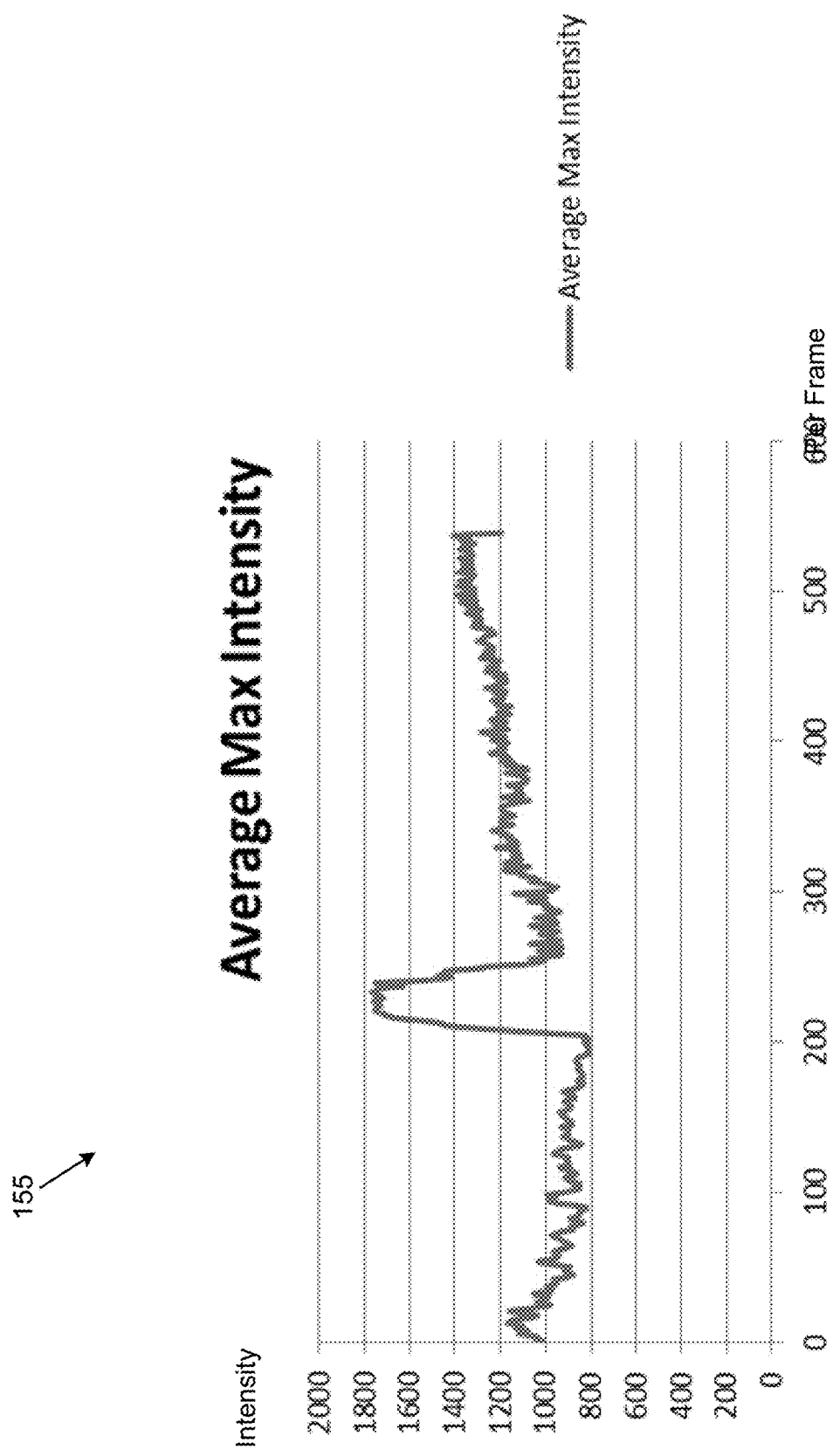
FIG. 6 is a plot of average maximum intensity per frame in which identification of the guide catheter is indeterminant in accordance with an illustrative embodiment of the disclosure.
Figure 7:
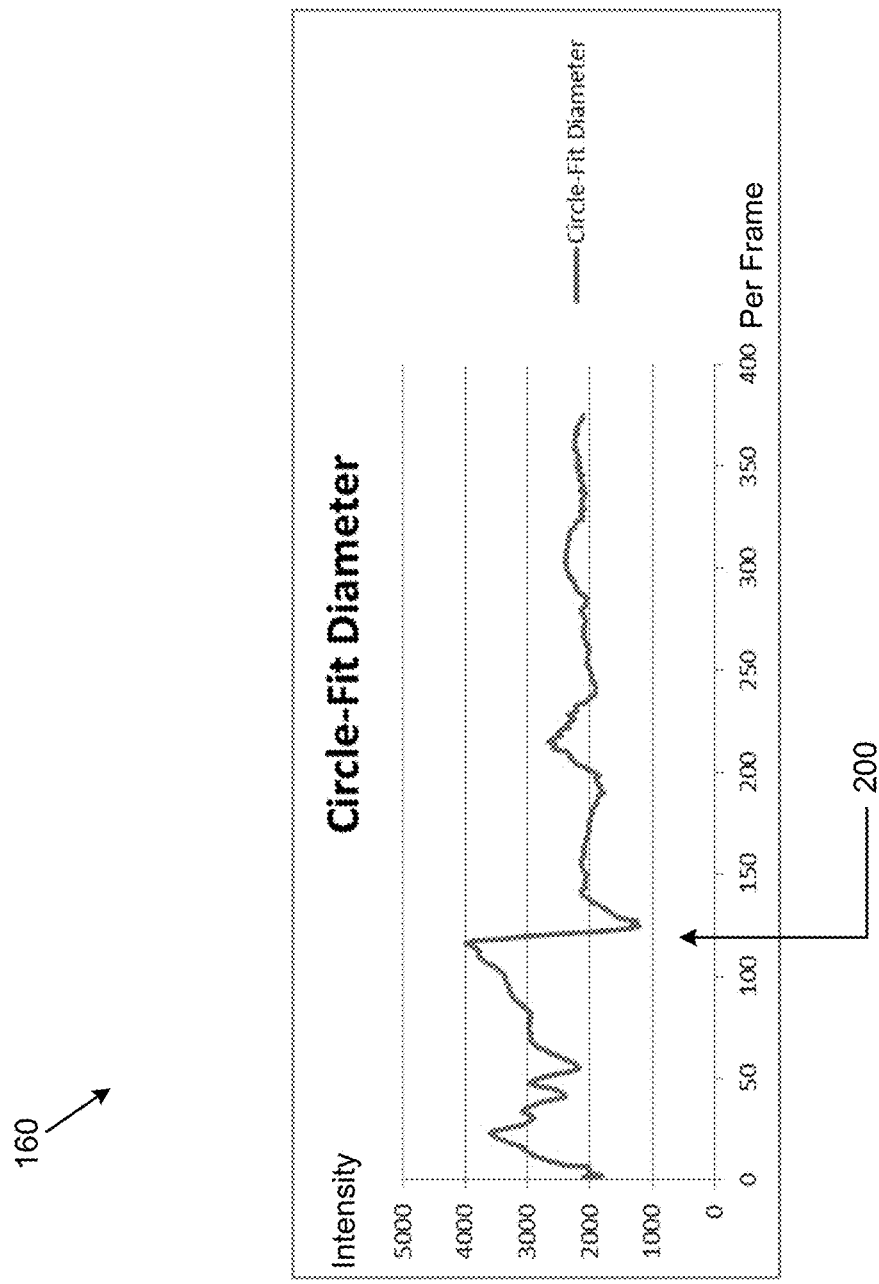
FIG. 7 is a plot of circle-fit diameter per frame in which a positive identification of the guide catheter has been achieved in accordance with an illustrative embodiment of the disclosure.

With regard to FIGS. 4, 6 and 7, the right hand side of the plot includes frames that contain the guide catheter such that imaging was performed through the guide catheter. In contrast, the left side of these plots includes frames that include the imaging of the lumen in which the imaging probe is not within the guide catheter.

Figure 5:
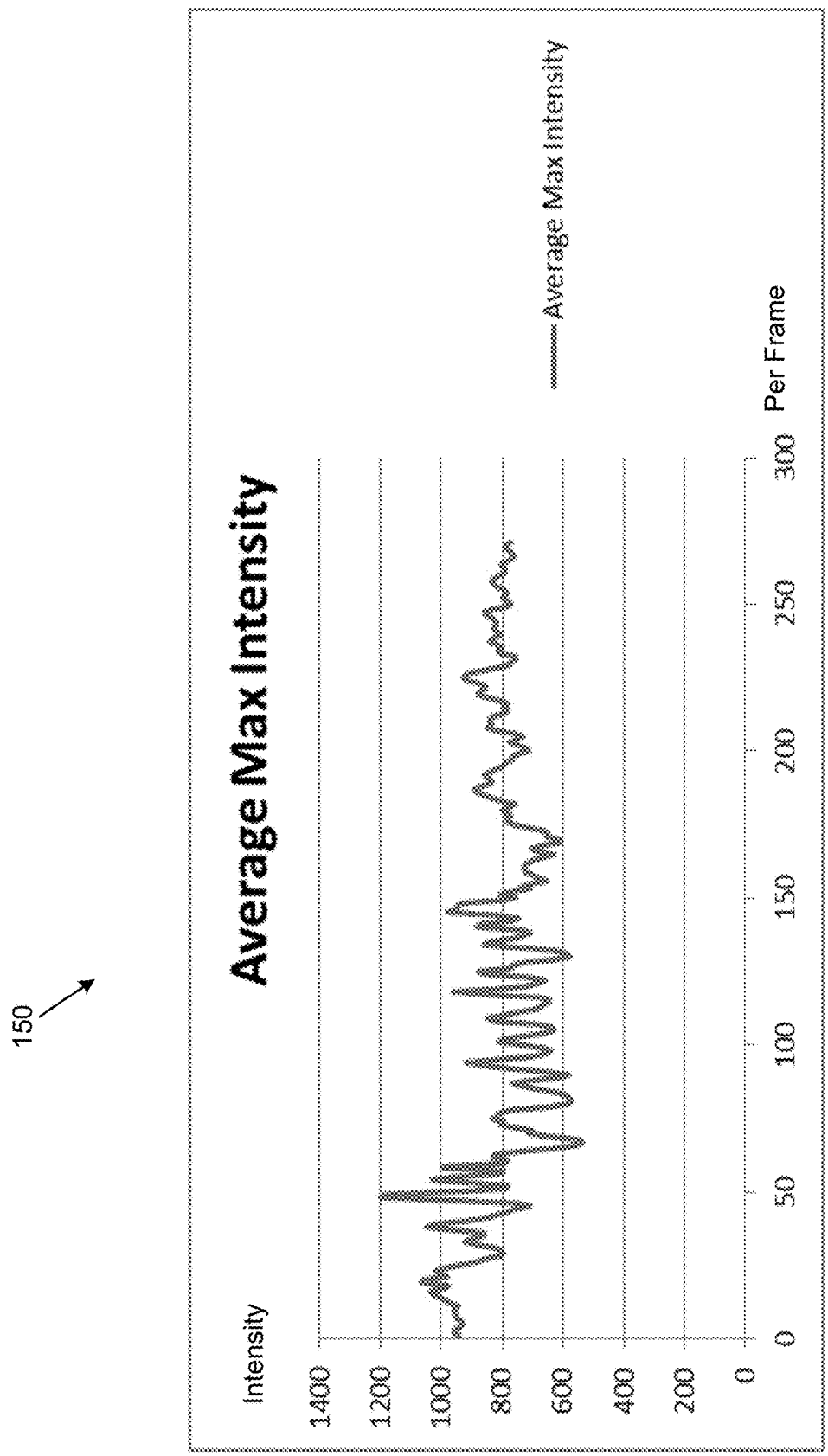
FIG. 5 is a plot of average maximum intensity per frame in which a negative identification of the guide catheter has been occurred in accordance with an illustrative embodiment of the disclosure.

In one embodiment, the GC detection method compares brightness or intensity levels such as shown with regard to FIG. 4. FIG. 4 shows a positive identification using an intensity based detection method for a pullback of about 300 frames. Average max intensity is plotted on a per frame basis as shown. The GC is detected around from 175 as shown by detection indicator 120. FIG. 4 shows a case of relatively ideal data with little noise or other signal artifacts. FIG. 5 shows an intensity versus pullback frame plot with a negative identification using an intensity-based detection method. Thus, in FIG. 5 a GC was not detected in the set of frames evaluated. In FIG. 6, the data is non-ideal and detection is indeterminate. That is, with regard to the frames evaluated in FIG. 6 shows an indeterminate case using an intensity-based detection method.

In the indeterminant case shown in FIG. 6, the intensity drop (scanning from right to left) represents a candidate frame for the tip of the catheter. Unfortunately, as shown in FIG. 6 there are two drops and a peak having a width that spans several frames. As a result, the detection processes described would not generate a usable output for the intensity data based approach for which the plot of FIG. 6 would apply. Given the occurrence of an indeterminant result, one of the other GC detection methods would be used or multiple GC methods in addition to an intensity approach would be run by the data collection system.

In one embodiment, as a sequence of methods to address the indeterminate scenarios in which one method cannot detect the GC, "average-max intensity" method is used as a primary method used. It provides good positive and negative results with most catheters and most cases. When its results are indeterminant the other methods are used to verify the result. Negative results are useful in that it provides a basis for assessing a pullback and determining that imaging did not continue into the guide catheter with regard to the frames of data analyzed.

Circle-Fit Detection Method

In one embodiment, the circle-fit detection method is based on one or more geometric or dimensional property. The circle-fit detection method identifies the tip of a catheter as the point or a range of points at which a diameter of the lumen undergoes a transition such a transition such as a drop, slope change, spike, or other identifiable intensity transition. In one embodiment, the transition is a sharp increase. In one embodiment, a lumen detection software module or method is used to determine a plurality of points of a lumen boundary for the lumen of the blood vessel in which the catheter is disposed. The diameter of the lumen is determined based on a goodness of fit test of a plurality of lumen boundary points to a set of points constrained to define a circle. The lumen boundary points can be determined on a per frame or per lumen segment basis using one or more lumen detection methods. In one embodiment, the goodness of fit test is based on a least-squares fit of the lumen boundary points to a circle.

The circle fit method looks for an increase in lumen diameter when scanning from the proximal end. On each frame the lumen diameter and circularity are measured using the binary image of the frame. In one embodiment, the method includes take all lumen points and mapping them to rectangular coordinates. These mapped points are then fit to a circle on a per frame basis using a regression based method. In one embodiment, the mapped points are collectively processed using a least-squares circle fit algorithm. In such a method, the sum of the squares of offset values is minimized to fit a set of mapped points in a given frame to a circle in that frame. The diameter of the modeled circle is recorded for each frame. If the diameter is consistent between frames such frames can be flagged or identified as including the GC. When a diameter deviation occurs those frames can be identified for further validation or identified as non-GC frames. Under some circumstance, the best fit circle may not contain any of the lumen points. Thus, the fit is determined on an aggregate basis. In one embodiment, a total residual error after the fit is computed, and is used to determine if the fit is good.

Scanning from the proximal end (right to left) to the distal end, results in a plot of each circle-fit diameter determined using the regression based approach as shown in FIG. 7. The scanning is performed from right to left as a result of the higher frame numbers corresponding to the end of the pullback sequence and the image frames that will include the guide catheter will be at the end or closer to end of the sequence of pull frames. Starting the scan of the data from the right, if there is a guide catheter present, the scan will start within the guide catherer and then encounter usable pullback image data. From the plot of FIG. 7, a diameter transition in the form of a sharp increase is seen at about frame 117. The detection method used relative to FIG. 7 is a circle fit-based method. A diameter increase is detected at frame 117 which corresponds to a transition from a consistent circular cross-section of the GC to an expanded distance of the lumen. This signature transition can be used to detect the GC in one embodiment.

In one embodiment, the frame corresponding to the GC tip is stored in one memory element and used to exclude the frames or scan lines that continue after it and include the guide catheter. After identifying the catheter tip candidate frame to frames to the proximal side are evaluated using a computing device such as a processor in communication with an intravascular data collection system to determine if they fit within a tolerance of one another. In one embodiment, a circularity criterion is also imposed on the candidates.

Chord-Histogram Detection Method

In one embodiment, the chord-histogram detection method is based on one or more geometric or dimensional property. The chord-histogram detection method identifies the tip of a catheter as the point or a range of points at which a diameter of the lumen undergoes a transition such a transition such as a drop, slope change, spike, or other identifiable intensity transition. In one embodiment, the transition of the lumen diameter is a sharp increase. In one embodiment, a lumen detection software module or method is used to determine a plurality of points of a lumen boundary for the lumen of the blood vessel in which the catheter is disposed.

The diameter of the lumen is determined based on a count, prevalence, score, or statistical analysis of a plurality of cords. In one embodiment, the plurality of chords includes one or more chords at each sampling angle in a frame of intravascular image data or the scan line representation thereof. The lumen boundary points can be determined on a per frame or per lumen segment basis using one or more lumen detection methods. In one embodiment, the median, mean, mode, or other statistically significant chord is selected as the diameter. In one embodiment, the most prevalent chord is selected as a diameter. The diameter or values described herein can be stored as an array or vector and processed by one or more software modules to perform the steps described herein.

Dominant Chord Method

Figure 9:
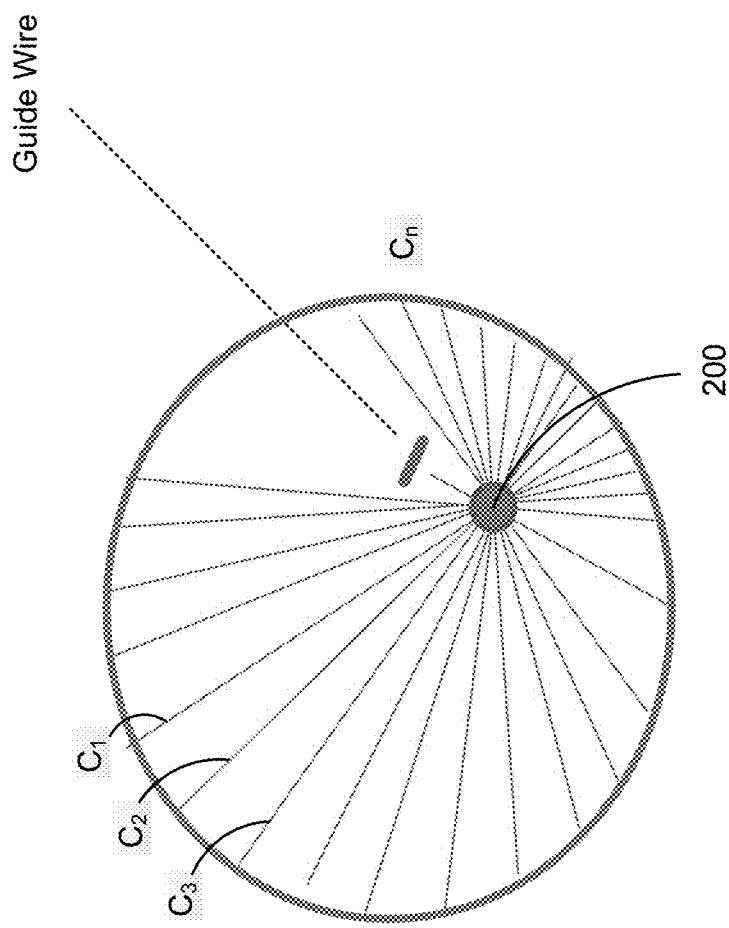
FIG. 9 is a schematic diagram of chords added to a histogram in accordance with an illustrative embodiment of the disclosure.

This method is similar to the Circle-Fit method except that the diameter is computed as the most dominant chord from the center of the image to the lumen edge. Since the lumen may not be centered in the image the lines through the center of the image form chords rather than diameters. It is useful to use a histogram or other statistical plot of the data or a score for each chord. In one embodiment, a histogram is generated or a representation thereof in an electronic memory device such as one or more matrices and a peak or other transition or relative extremum of the histogram is selected as an approximation of the diameter of the guide catheter. FIG. 9 shows an exemplary set of chords that can be added to such a histogram to select the dominant chord as a diameter measure for the GC.

In one embodiment, the image data processing modules, such as the lumen detection module, or a precursor to it can generate a binary mask of the image such that regions of tissue (or other non-lumen areas) are set at one value such as one or white or another value and the lumen regions are identified in the mask by another value such as zero or black or another value. Thus, two values are used in the mask to identify different categories of features.

In one embodiment, the image processing software can identify various points, frames, pairs of points within each frame. In one embodiment, the software module can operate open or otherwise transform the previously generated binary mask representation to identify start stop pairs. These start stop pairs can refer to the start and stop of runs of a set of pixels in the binary image of the lumen.

The diameter is estimated by generating a set of possible chords such as a set of all possible chords or a subset thereof and selecting the most dominant chord. Additionally, the concept of using transitions between different regions in the form of start and stop pairs can also be used. A start sample or start point or region indicates the start of a tissue region in a scan line or a region of a frame. Similarly, a stop sample or stop point or region indicates the end of a tissue region. The start of a tissue region and the end of a tissue region can be referred to as a stop and start pair (or vice versa) and can be referred to as a SS-Pair. In one embodiment, for every angle, $\alpha$, from 0 to 180° all combinations of stop and start pairs (also referred to herein as SS-Pairs) for the scan lines corresponding to $\alpha$ and $\alpha+180$ are considered. Alternatively, in one embodiment, for a plurality of angles, $\alpha$, such as sampling of N angles from 0 to 180°, a plurality of combinations of SS-Pairs for the scan lines corresponding to $\alpha$ and $\alpha+180$ are considered.

Figure 8:
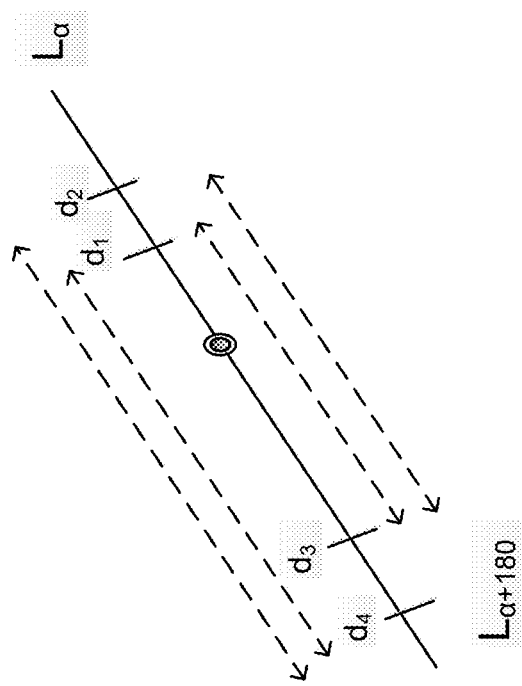
FIG. 8 is a schematic diagram of chords per line in accordance with an illustrative embodiment of the disclosure.

As an example, two scan lines $L_{\alpha+180}$ and $L_{\alpha}$ are shown in the schematic representation of this selection shown in FIG. 8. The various distances of the chords are recorded and are stored as a data representation such as a histogram. For example, if the scan line corresponding to angle $\alpha$ ($L_{\alpha}$) has two start-stop pairs with length from center of $d_1$ and $d_2$, and the corresponding scan line has SS pairs at distances $d_3$ and $d_4$, then the lengths $(d_1+d_3)$, $(d_1+d_4)$, $(d_2+d_3)$, and $(d_2+d_3)$ are all added to the histogram of diameters.

For each angle from 0 to 180° the chords are added to the histogram as shown in FIG. 9. In the Figure various chords $C_1$, $C_2$, $C_3$ through $C_N$ radiate out from point 200. In the example with only a single chord length per scan line pair, all the lengths of the blue chords are added to the histogram. The regions where a guide wire is present will necessarily create short chords.

Once a set of chords is added to the histogram, as shown in FIG. 9, in one embodiment the histogram it is smoothed using a boxcar average (running average) filter. With this set of transformed information, following the application of the filter, the peak is identified in the smoothed histogram. This peak is selected as an approximation of the diameter for this frame. Once all frames are scored or otherwise processed as described herein to select a diameter on a per frame basis from the set of chords for that frame, the overall set of selected diameters is evaluated moving across the frames. Thus, looking at FIG. 7 and moving from right to left through the plot of diameters versus frames a point or range of points corresponding to the transition associated with the guide catheter is identified by the software. The same analysis as in the "Circle-Fit" method is performed to identify the candidate catheter tip position or GC containing frames.

Circle-Histogram/Dominant Circle Detection Method

In one embodiment, the circle-histogram detection method is based on one or more geometric or dimensional property. The circle-histogram method includes a subset of features of one or both of the circle-fit method and the circle-histogram method. The circle-histogram detection method identifies the tip of a catheter as the point or a range of points at which a diameter measure undergoes a transition such a transition such as a drop, slope change, spike, or other identifiable intensity transition. In one embodiment, the transition of the lumen diameter is a sharp increase. In one embodiment, a lumen detection software module or method is used to determine a plurality of points of a lumen boundary for the lumen of the blood vessel in which the catheter is disposed. The diameter measure is determined based on fitting three or more equally spaced points on the lumen boundary. In one embodiment, the points are constrained to define a circle goodness of fit test of a plurality of lumen boundary points to a set of points constrained to define a circle. In one embodiment, the method uses three equally spaced points on the lumen to fit a circle whose diameter is used for that frame.

The diameter of the lumen is determined based on a count, prevalence, score, or statistical analysis of a plurality of cords. In one embodiment, the plurality of chords includes one or more chords at each sampling angle in a frame of intravascular image data or the scan line representation thereof. The lumen boundary points can be determined on a per frame or per lumen segment basis using one or more lumen detection methods. In one embodiment, the median, mean, mode, or other statistically significant chord is selected as the diameter. In one embodiment, the most prevalent chord is selected as a diameter.

The circle-histogram/dominant circle detection method include several steps that are substantially the same as the dominant chord method with a few exceptions. Specifically, instead of using one or more chords as a geometric parameter, in the dominant circle detection one ore more diameters of one or more circles are used in lieu of one or more chords. With respect to each circle, the circle is fit to the lumen boundary determined using one or more lumen detection methods. In one embodiment, each such circle is fit to three points on the lumen boundary. In one embodiment, the points are spaced equally and thus define sectors having congruent angles. On a given frame, for each scan line three lumen points are identified 120 degrees apart. The diameter of the circle passing through these three points is used to determine the diameter for scoring the frame. The remaining logic is the same as the previous method.

Figure 10:
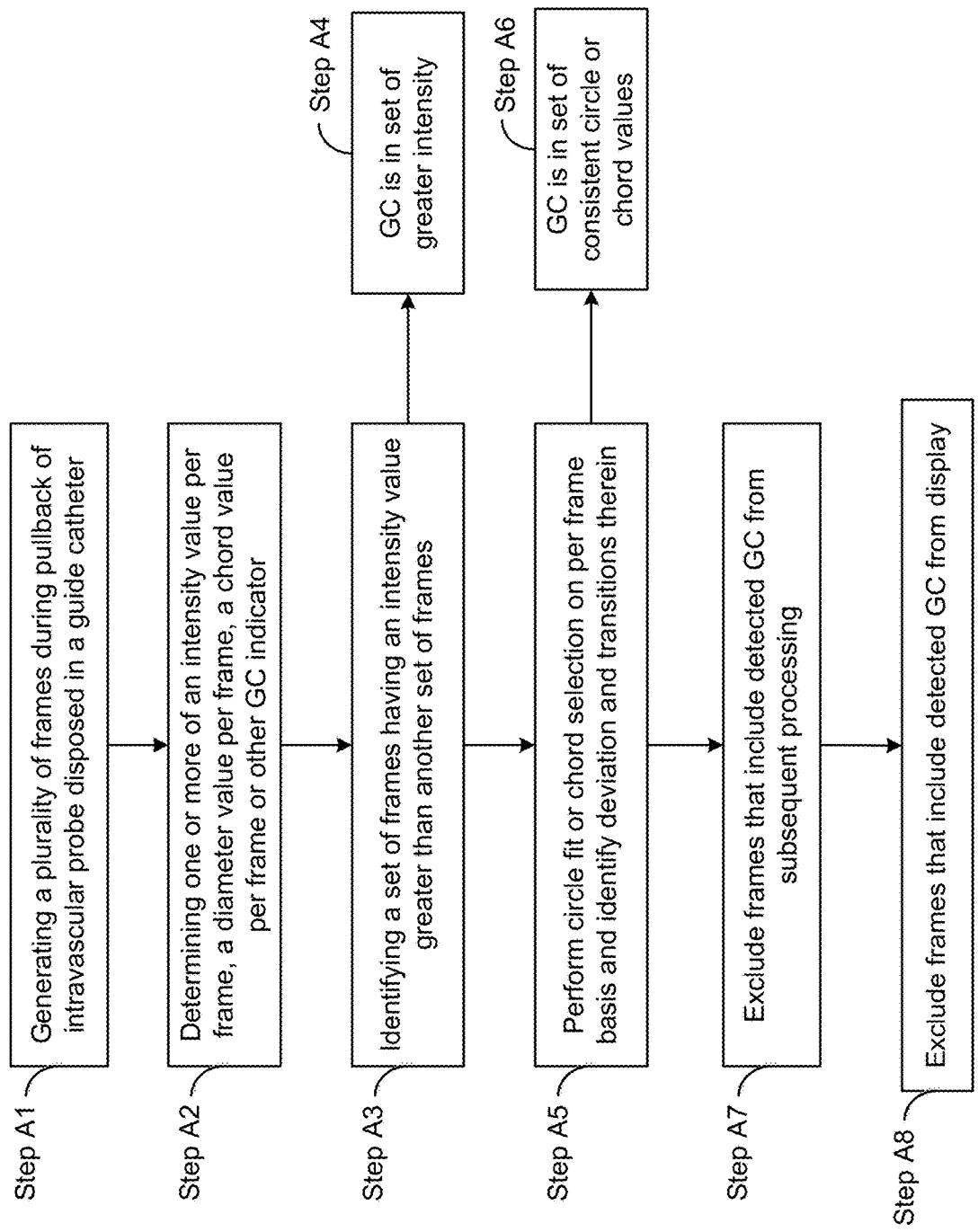
FIG. 10 is a method of detecting a guide catheter in accordance with an illustrative embodiment of the disclosure.

FIG. 10 is a method of detecting a guide catheter in accordance with an illustrative embodiment of the disclosure. FIG. 10 includes an overview of the methods and steps described herein. All of the steps need not be performed and some detection steps can be used to validate others in the case of indeterminate results. The method includes generating a plurality of frames during pullback of intravascular probe disposed in a guide catheter Step A1. Determining one or more of an intensity value per frame, a diameter value per frame, a chord value per frame or other GC indicator Step A2 is performed in one or more embodiments. Identifying a set of frames having an intensity value greater than another set of frames is performed in one or more embodiments Step A3. If a GC is present, it will be detected in the set of greater intensity Step A4. The method can include performing a circle fit or chord selection on per frame basis and identify deviation and transitions therein Step A5. If a GC is present, it will be detected in set of consistent circle or chord values Step A6. In some embodiments, GC results in certain steps or downstream image processing being performed with GC containing frames excluded. In other methods, the GC frames are not excluded. In one embodiment, the method excludes frames that include detected GC from subsequent processing Step A7. In one embodiment, the method excludes frames that include detected GC from being displayed Step A8 such as on a cath lab device or system or other devices or displays.

Non-Limiting Software Features and Embodiments for Implementing Guide Catheter Detection The following description is intended to provide an overview of device hardware and other operating components suitable for performing the methods of the disclosure described herein. This description is not intended to limit the applicable environments or the scope of the disclosure. Similarly, the hardware and other operating components may be suitable as part of the apparatuses described above. The disclosure can be practiced with other system configurations, including personal computers, multiprocessor systems, microprocessor-based or programmable electronic device, network PCs, minicomputers, mainframe computers, and the like. The disclosure can also be practiced in distributed computing environments where tasks are performed by remote processing devices that are linked through a communications network such as in different rooms of a catheter or cath lab.

Some portions of the detailed description are presented in terms of algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

Unless specifically stated otherwise as apparent from the following discussion, it is appreciated that throughout the description, discussions utilizing terms such as "processing" or "computing" or "searching" "sampling" or "detecting" or "measuring" or "calculating" or "comparing" "generating" or "determining" or "displaying," or Boolean logic or other set related operations or the like, refer to the action and processes of a computer system, or electronic device, that manipulates and transforms data represented as physical (electronic) quantities within the computer system's or electronic devices' registers and memories into other data similarly represented as physical quantities within electronic memories or registers or other such information storage, transmission or display devices.

The present disclosure, in some embodiments, also relates to apparatus for performing the operations herein. This apparatus may be specially constructed for the required purposes, or it may comprise a general purpose computer selectively activated or reconfigured by a computer program stored in the computer.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below. In addition, the present disclosure is not described with reference to any particular programming language, and various embodiments may thus be implemented using a variety of programming languages.

Embodiments of the disclosure may be embodied in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other programmable logic device), discrete components, integrated circuitry (e.g., an Application Specific Integrated Circuit (ASIC)), or any other means including any combination thereof. In a typical embodiment of the present disclosure, some or all of the processing of the data collected using an OCT probe and the processor-based system is implemented as a set of computer program instructions that is converted into a computer executable form, stored as such in a computer readable medium, and executed by a microprocessor under the control of an operating system. Thus, query response and input data are transformed into processor understandable instructions suitable for generating OCT data, detecting lumen borders, detecting guide catheters and optical signatures relating thereto, comparing measured perpendicular distances relative to set thresholds, and otherwise performing image comparison, signal processing, artifact removal, and other features and embodiments described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Various examples of suitable processing modules are discussed below in more detail. As used herein a module refers to software, hardware, or firmware suitable for performing a specific data processing or data transmission task. Typically, in a preferred embodiment a module refers to a software routine, program, or other memory resident application suitable for receiving, transforming, routing and processing instructions, or various types of data such as OCT scan data, interferometer signal data, guide wire locations, shadow region locations, side branch locations, side branch diameters, intensity profiles, and other information of interest.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the disclosure described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the disclosure.

A storage medium may be non-transitory or include a non-transitory device. Accordingly, a non-transitory storage medium or non-transitory device may include a device that is tangible, meaning that the device has a concrete physical form, although the device may change its physical state. Thus, for example, non-transitory refers to a device remaining tangible despite this change in state.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus.

Embodiments may include various steps, which may be embodied in machine-executable instructions to be executed by a computer system. A computer system includes one or more general-purpose or special-purpose computers (or other electronic devices). The computer system may include hardware components that include specific logic for performing the steps or may include a combination of hardware, software, and/or firmware.

Embodiments may also be provided as a computer program product including a computer-readable medium having stored thereon instructions that may be used to program a computer system or other electronic device to perform the processes described herein. The computer-readable medium may include, but is not limited to: hard drives, floppy diskettes, optical disks, CD-ROMs, DVD-ROMs, ROMs, RAMs, EPROMs, EEPROMs, magnetic or optical cards, solid-state memory devices, or other types of media/computer-readable media suitable for storing electronic instructions.

Each computer system includes at least a processor and a memory; computer systems may also include various input devices and/or output devices. The processor may include a general purpose device, such as an Intel, AMD, or other "off-the-shelf" microprocessor. The processor may include a special purpose processing device, such as an ASIC, SoC, SiP, FPGA, PAL, PLA, FPLA, PLD, or other customized or programmable device. The memory may include static RAM, dynamic RAM, flash memory, one or more flip-flops, ROM, CD-ROM, disk, tape, magnetic, optical, or other computer storage medium. The input device(s) may include a keyboard, mouse, touch screen, light pen, tablet, microphone, sensor, or other hardware with accompanying firmware and/or software. The output device(s) may include a monitor or other display, printer, speech or text synthesizer, switch, signal line, or other hardware with accompanying firmware and/or software.

The computer systems may be capable of using a floppy drive, tape drive, optical drive, magneto-optical drive, or other means to read a storage medium. A suitable storage medium includes a magnetic, optical, or other computer-readable storage device having a specific physical configuration. Suitable storage devices include floppy disks, hard disks, tape, CD-ROMs, DVDs, PROMs, random access memory, flash memory, and other computer system storage devices. The physical configuration represents data and instructions which cause the computer system to operate in a specific and predefined manner as described herein.

Suitable software to assist in implementing the invention is readily provided by those of skill in the pertinent art(s) using the teachings presented here and programming languages and tools, such as Java, C++, C, database languages, APIs, SDKs, assembly, firmware, microcode, and/or other languages and tools. Suitable signal formats may be embodied in analog or digital form, with or without error detection and/or correction bits, packet headers, network addresses in a specific format, and/or other supporting data readily provided by those of skill in the pertinent art(s).

Several aspects of the embodiments described will be illustrated as software modules or components. As used herein, a software module or component may include any type of computer instruction or computer executable code located within a memory device. A software module may, for instance, include one or more physical or logical blocks of computer instructions, which may be organized as a routine, program, object, component, data structure, etc. that perform one or more tasks or implement particular abstract data types.

A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending data, images, and other information to and receiving the same from a device that is used by the user.

The aspects, embodiments, features, and examples of the disclosure are to be considered illustrative in all respects and are not intended to limit the disclosure, the scope of which is defined only by the claims. Other embodiments, modifications, and usages will be apparent to those skilled in the art without departing from the spirit and scope of the claimed disclosure.

The use of headings and sections in the application is not meant to limit the disclosure; each section can apply to any aspect, embodiment, or feature of the disclosure.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise. As used herein, the term "about" refers to a ±10% variation from the nominal value.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the disclosure as if each value were specifically enumerated herein. In addition, smaller ranges between and including the upper and lower limits of a given range are contemplated and encompassed within the disclosure. The listing of exemplary values or ranges is not a disclaimer of other values or ranges between and including the upper and lower limits of a given range.

It is to be understood that the figures and descriptions of the disclosure have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the disclosure, a single component may be replaced by multiple components, and multiple components may be replaced by a single component, to provide an element or structure or to perform a given function or functions. Except where such substitution would not be operative to practice certain embodiments of the disclosure, such substitution is considered within the scope of the disclosure.

The examples presented herein are intended to illustrate potential and specific implementations of the disclosure. It can be appreciated that the examples are intended primarily for purposes of illustration of the disclosure for those skilled in the art. There may be variations to these diagrams or the operations described herein without departing from the spirit of the disclosure. For instance, in certain cases, method steps or operations may be performed or executed in differing order, or operations may be added, deleted or modified.

What is claimed is:

1. A method of a detecting a guide catheter disposed in a lumen of a blood vessel, the method comprising:
    collecting a set of scan lines using a probe disposed in the blood vessel and positioned using the guide catheter;
    determining a maximum intensity value for each scan line in a set of frames;
    averaging maximum intensity values of scan lines for each frame of the set of frames; and
    identifying one or more frames from the set of frames as containing the guide catheter based upon the average maximum intensity value of the one or more frames being greater than the average maximum intensity value of other frames in the set of frames.

2. The method of claim 1 further comprising the step of identifying intravascular data that includes the guide catheter and excluding such intravascular data when performing stent detection.

3. The method of claim 1 further comprising the step of identifying intravascular data that includes the guide catheter and excluding such intravascular data when performing shadow detection.

4. A method of a detecting a guide catheter disposed in a blood vessel, the method comprising:
    collecting scan lines using an intravascular probe disposed in the blood vessel, the probe positioned using the guide catheter;
    determining maximum intensity values on a per scan line basis, using an imaging system, for a set of frames;
    averaging the maximum intensity values of scan lines on a per frame basis;
    determining, a group of the average maximum intensity values for a subset of the frames, using the imaging system, that are greater than the average maximum intensity values of other frames in the set of frames; and
    identifying one or more frames of the subset of frames as corresponding to guide catheter containing frames.

5. The method of claim 4 further comprising excluding intravascular data that includes one or more elements that correspond to the guide catheter when performing stent detection.

6. The method of claim 4 further comprising excluding intravascular data that includes one or more elements that correspond to the guide catheter when performing shadow detection.

* * * * *